United States Patent
Shell et al.

(10) Patent No.: US 6,340,475 B2
(45) Date of Patent: *Jan. 22, 2002

(54) EXTENDING THE DURATION OF DRUG RELEASE WITHIN THE STOMACH DURING THE FED MODE

(75) Inventors: John W. Shell, Hillsborough; Jenny Louie-Helm, Union City; Micheline Markey, Santa Cruz, all of CA (US)

(73) Assignee: DepoMed, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/282,233

(22) Filed: Mar. 29, 1999

Related U.S. Application Data

(63) Continuation-in-part of application No. 08/870,509, filed on Jun. 6, 1997, now abandoned.

(51) Int. Cl.[7] .............................. A61K 9/26; A61K 9/14
(52) U.S. Cl. ...................... 424/469; 424/464; 424/468; 424/488; 424/486; 424/487
(58) Field of Search .............................. 424/451, 457, 424/458, 464, 468, 469, 484, 485, 486, 489, 501, 502, 426

(56) References Cited

U.S. PATENT DOCUMENTS

| | | |
|---|---|---|
| 5,007,790 A | 4/1991 | Shell |
| 5,273,758 A | 12/1993 | Royce |
| 5,582,837 A | 12/1996 | Shell |
| 5,591,452 A | 1/1997 | Miller et al. |
| 5,972,389 A * | 10/1999 | Shell et al. |

FOREIGN PATENT DOCUMENTS

| | | |
|---|---|---|
| DE | 44 32 757 A | 3/1996 |
| EP | 0 761 209 A | 3/1997 |
| WO | 90/11757 | 10/1990 |
| WO | 93/18755 | 9/1993 |
| WO | 96/32097 | 10/1996 |
| WO | 98/11879 | 3/1998 |
| WO | 98/55107 | 12/1998 |

OTHER PUBLICATIONS

A. Apicella et al. *Biomaterials* (1993) 14(2):83–90.

* cited by examiner

Primary Examiner—Thurman K. Page
Assistant Examiner—Brian K. Seidleck
(74) Attorney, Agent, or Firm—Townsend and Townsend and Crew LLP

(57) ABSTRACT

Drugs are formulated as unit oral dosage forms by incorporating them into polymeric matrices comprised of hydrophilic polymers that swell upon imbibition of water to a size that is large enough to promote retention of the dosage form in the stomach during the fed mode. The oral formulation is designed for gastric retention and controlled delivery of an incorporated drug into the gastric cavity, and thus administered, the drug is released from the matrix into the gastric fluid by solution diffusion. The swollen polymeric matrix, having achieved sufficient size, remains in the gastric cavity for several hours if administered while the patient is in the fed mode, and remains intact long enough for substantially all of the drug to be released before substantial dissolution of the matrix occurs. The swelling matrix lowers the accessibility of the gastric fluid to the drug and thereby reduces the drug release rate. This process, together with diffusion retardation by selection of specific polymers, polymer molecular weights, and other variables, results in a sustained and controlled delivery rate of the drug to the gastric cavity.

89 Claims, 9 Drawing Sheets

EXTENDING THE DURATION OF DRUG RELEASE WITHIN THE STOMACH DURING THE FED MODE

CROSS-REFERENCE TO RELATED APPLICATION

This application is a continuation-in-part of application Ser. No. 08/870,509, filed Jun. 6, 1997 now abandoned, the entire contents of which are hereby incorporated herein by reference.

This invention is in the general field of pharmacology, and relates in particular to formulations for drugs that benefit from a prolonged time of controlled release in the stomach and upper gastrointestinal (GI) tract, and from an enhanced opportunity of absorption in the stomach and upper GI tract rather than the lower portions of the GI tract. One goal in this invention is to release highly soluble drugs in a controlled manner over an extended period of time. Another goal is to extend the time of delivery into the stomach of drugs that are preferentially absorbed high in the GI tract, for purposes of achieving a greater and more prolonged therapeutic effect and thus reducing the frequency of administration required; a more efficient use of the drugs; and a more effective treatment of local stomach disorders. Another goal is to minimize both lower-tract inactivation of the drug and drug effects on the lower intestinal flora by confining the delivery and absorption of the drug to the upper GI tract.

BACKGROUND OF THE INVENTION

Drugs that are administered in the form of conventional tablets or capsules become available to body fluids at a rate that is initially very high, followed by a rapid decline. For many drugs, this delivery pattern results in a transient overdose, followed by a long period of underdosing. This is a pattern of limited clinical usefulness. The delivery pattern was improved in the 1970's with the introduction of a variety of controlled delivery systems. By providing relatively constant, controlled drug delivery, these systems avoided the overdose and the underdose effects. These improvements provided effective medication with reduced side effects, and achieved these results with reduced dosing frequency.

Many of these controlled delivery systems utilize hydrophilic, polymeric matrices that provide useful levels of control to the delivery of sparingly soluble drugs. For soluble drugs, however, and particularly for highly soluble drugs, such matrices do not provide adequate control over the drug release rate, instead resulting in a release that approximates first-order kinetics. That is, the rate of release is an inverse function of the square root of the elapsed time. With this pattern of release, most of the drug in the matrix is often released within the first hour in an aqueous medium.

One method of prolonging the release of a highly water-soluble drug is disclosed in International Patent Application Publication No. WO 96/26718, published Sep. 6, 1996 (applicant: Temple University; inventor: Kim). The method of this publication is the incorporation of the drug into a polymeric matrix to form a tablet that is administered orally. The polymer is water-swellable yet erodible in gastric fluids, and the polymer and the proportion of drug to polymer are chosen such that:

(i) the rate at which the polymer swells is equal to the rate at which the polymer erodes, so that the swelling of the polymer is continuously held in check by the erosion, and zero-order release kinetics (constant delivery rate) of the drug from the matrix are maintained;

(ii) the release of drug from the matrix is sustained over the full erosion period of the polymer, the tablet therefore reaching complete solution at the same time that the last of the drug is released; and (iii) release of the drug from the matrix will be extended over a period of 24 hours.

A key disclosure in WO 96/26718 is that to achieve the release of drug in this manner requires the use of a low molecular weight polymer. If, by contrast, a high molecular weight polymer is used and the swelling rate substantially exceeds the erosion rate, the lack of erosion will prolong even further the delivery of the drug residing close to the center of the tablet and even prevent it from being released. Thus, there is no disclosure in WO 96/26718 that a drug of high water solubility can be released from a high molecular weight polymer in a period of time substantially less than 24 hours, or that any advantage can be obtained by the use of a polymer that does not erode as quickly as it swells. This failure is particularly significant since even swollen tablets will not remain in the stomach beyond the duration of the fed mode, which typically lasts for only 4 to 6 hours.

For drugs of any level of solubility, the retention of the drug in a tablet or other dosage form beyond the duration of the fed mode raises a number of problems that detract from the therapeutic efficacy of the drug. These problems arise from the tendency of the tablet when the patient is no longer in the fed mode to pass from the stomach into the small intestine, and over a period of 2–4 hours to pass through the small intestine, thus reaching the colon with the drug still in the tablet. This loss of effectiveness occurs with drugs that provide their maximum benefit with minimum side effects when absorbed in the stomach and upper GI tract rather than the colon. The reasons are either favorable conditions in the stomach, unfavorable conditions in the colon, or both.

For example, most orally administered antibiotics have a potential of altering the normal flora of the gastrointestinal tract, and particularly the flora of the colon. One result of these alterations is the overgrowth of the organism *Clostridium difficile,* which is a serious adverse event since this organism releases dangerous toxins. These toxins can cause pseudomembranous colitis, a condition that has been reported as a side effect of the use of many antibiotics. In its milder forms, pseudomembranous colitis can cause mild nausea and diarrhea while in its stronger forms, it can be life-threatening or fatal. Examples of highly soluble antibiotics that pose this type of threat are amoxicillin, cefuroxime axetil, and clindamycin. Cefuroxime axetil (i.e., the axetil ester of cefuroxime), for example, becomes active when hydrolyzed to free cefuroxime, but when this occurs prior to absorption, it can be detrimental to essential bacterial flora. Hydrolysis to the active form typically occurs in the tissues into which the ester has been absorbed, but if the ester reaches the lower intestine, enzymes in the lower intestine cause the hydrolysis to occur in the intestine itself, which not only renders the drug unabsorbable but also converts the drug to the active form where its activity alters the flora. Examples of sparingly soluble antibiotics that pose the same type of threat are clarithromycin, azithromycin, ceftazidine, ciprofloxacin, and cefaclor.

A goal of the present invention is to avoid this type of alteration of the lower intestinal flora by delivering antibiotics, regardless of their level of solubility, in a manner that confines their delivery to the stomach and upper small intestine. Slow, continuous delivery from a gastric retentive system assures that both drug delivery and drug absorption are confined to the upper GI tract. More efficient delivery of antibiotics will also avoid transient overdosing which is a major cause of overgrowth of *Clostridium difficile.*

Another example is the class of drugs that are susceptible to degradation by exposure to gastric fluid, either by enzymes or low solution pH. The swellable hydrophilic matrix of the present invention protects the yet undelivered drug during the 4 to 6 hour delivery period during which the drug is continuously released while the dosage form is retained in the stomach. One example of such a drug is topiramate, a drug that is used for the treatment of epilepsy. Topiramate is absorbed preferentially high in the GI tract and is hydrolyzed by the acidic environment of the stomach. The dosage form and delivery system of the present invention will confine the delivery of the drug to the stomach and duodenum. As the drug diffuses out of the swollen matrix, it is susceptible to the acidic environment, but the undelivered drug is protected from degradation by the polymer matrix.

Another example is the class of drugs that are known to have an absorption window high in the GI tract, but are incompletely absorbed or have a wide absorption range, intrapatient as well as interpatient. One example of such a drug is cyclosporine, a drug of low solubility that is used as an immunosuppressant to reduce organ rejection in transplant surgery. In addition to this problem, cyclosporine is in general only incompletely absorbed (on the average around 30%), and the degree of absorption is highly variable from one patient to the next (ranging from about 5% to about 89%). The variability can be attributed in part to differences among the various disease states existing in the patients to whom the drug is administered, and differences in the length of time between the transplant surgery and the administration of the drug. The variability can also however be attributed to the poor aqueous solubility of the drug and to variations in the gastric emptying, variations in the length of time required for intestinal transit between the stomach and the colon, variations in mesenteric and hepatic blood flow, variations in lymph flow, variations in intestinal secretion and fluid volume, variations in bile secretion and flow, and variations in epithelial cell turnover. All of these variations are addressed by the dosage form and delivery system of the present invention, which by confining drug delivery to the stomach reduces these differences and maximizes the absorption of the cyclosporine.

Another example is the class of drugs that are susceptible to degradation by intestinal enzymes. The degradation occurs before the drug can be absorbed through the intestinal wall, leaving only a fraction of the administered dose available for the intended therapeutic action.

An example of a highly soluble drug that is susceptible to degradation by intestinal enzymes is the pro-drug doxifluridine (5'-deoxy-5-fluouridine (dFUR)). The activity of doxifluridine depends on its activation to 5-fluorouracil by pyrimidine nucleoside phosphorylases. These enzymes are found in tumors as well as in normal tissues, with their highest activity being in the small intestine. The activity of these enzymes in tumor cells is more than twice that of normal tissues. When doxifluridine is administered orally, it can be converted to 5-fluorouracil in the intestine before it reaches the tumors. 5-Fluorouracil is much more toxic than doxifluridine and causes intestinal toxicity (nausea and diarrhea) and severe damage to the intestinal villi. A goal of the present invention is to confine the absorption of doxifluridine to the stomach and upper GI tract, thereby avoiding or reducing its conversion to 5-fluorouracil and the attendant toxicity risk. A similar result is sought for other drugs with similar susceptibilities, such as cyclosporine and digoxin.

Another class of drugs whose effectiveness suffers when the drugs are not fully absorbed high in the GI tract are those that are susceptible to inactivation by drug transporters that reside in lower gastrointestinal tract enterocytes. The inactivation occurs before the drug penetrates the intestinal wall, here again leaving only a fraction of the administered dose available for the intended therapeutic action. One example of a drug transporter is the p-glycoprotein efflux system, in which a p-glycoprotein acts as an absorption barrier to certain drugs that are substrates for the p-glycoprotein. The barrier acts by attaching to these drugs and transporting them drug back into the lumen, e.g., the stomach, duodenum, jejunum/ileum or colon, from which they were absorbed, or preventing them from being absorbed at all. This restriction of the drug to the interior of the GI tract is effectively an inactivation of the drug if the drug must pass out of the GI tract into the bloodstream to be effective. The p-glycoprotein efflux system is useful in many respects, such as preventing toxic compounds from entering the brain. It interferes however in some cases with the efficacy of certain drugs that would otherwise be absorbed. The p-glycoprotein concentration is lowest in the stomach and increases in concentration down the GI tract to the colon where the p-glycoprotein is most prevalent. The dosage form of the present invention will release the drug over an extended period into the upper GI tract where p-glycoprotein is lowest.

Cyclosporine is an example of a drug of low solubility that is susceptible to inactivation by the p-glycoprotein efflux system, in addition to its susceptibility to degradation by colonic bacterial enzymes. Other examples of drugs of low solubility that are susceptible to the p-glycoprotein efflux system are the anti-cancer drug paclitaxel, ciprofloxacin, and the HIV protease inhibitors saquinavir, ritonavir, and nelfinavir. All of these drugs will benefit through preserved activity by the present invention.

A still further class of drugs that suffer in effectiveness when not fully absorbed before reaching the colon are drugs that require an acidic environment for effective bioavailability. For certain drugs, the pH at a given site within the GI tract is an essential determinant of the bioavailability of the drug, since the solubility of the drug varies with pH. The stomach has a low pH and hence an acidic environment, while the small intestine has a higher pH and hence an alkaline environment. Higher bioavailability is achieved in some cases by higher solubility, which with some drugs occurs in a more acidic environment, and in other cases by keeping the drugs in a non-ionized state that is necessary for absorption, which with some drugs also occurs in a more acidic environment. Acidic drugs that have a low pK, for example, are in the neutral form that is required for absorption and are therefore preferentially absorbed in the stomach. Examples of highly soluble drugs that achieve their highest bioavailability at a low pH are esters of ampicillin. Examples of low solubility drugs that behave similarly are iron salts, digoxin, ketoconazole, fluconazole, griseofulvin, itraconazole, and micoconazole. A further goal of the present invention is therefore to maximize the bioavailability of drugs of these types by confining them to the acidic environment of the stomach while controlling their release rate to achieve an extended release profile. The invention thus improves the efficiency of iron salts in the treatment of the various forms of anemia, the efficiency of digoxin in the treatment of the heart disease, and the efficiency of ketoconazole in the treatment of systemic fungal infections such as candidiasis, canduria, blastomycosis, coccidiomycosis, histoplasmosis, chronomycosis, and pacococcidiomycosis.

The invention also improves the efficiency of drugs that have at least one ionized group in the pH range of 5 through 8. Since this is the pH range encountered in the small intestine and the region of the colonic junction and ionized drugs are less absorbable than neutral drugs, this invention improves the absorption of these drugs by retaining them in the stomach environment. The invention also improves the efficiency of drugs that are degradable in an acidic environment such as that of the stomach by protecting them from the acidic environment until they are released from the dosage form, thereby reducing the duration of their exposure to the acidic environment.

A still further example of drugs that lose their efficacy upon reaching the lower portions of the GI tract are drugs that are soluble in an acidic environment but insoluble in an alkaline environment. The HIV protease inhibitor nelfinavir mesylate is one example of such a drug. Portions of the drug that are undissolved cannot be absorbed. Portions that are dissolved but not yet absorbed when they pass from the stomach into the small intestine may undergo precipitation and loss of their therapeutic benefit. This is confirmed by the fact that the presence of food in the GI tract substantially increases the extent of absorption of oral nelfinavir. Peak plasma concentration and area under the plasma concentration-time curve of nelfinavir are two-fold to three-fold greater when doses are administered with or following a meal. This is presumably due, at least in part, to enhanced retention of the drug in the stomach. A further goal of the present invention is therefore to provide a means of administering these drugs that will maximize their therapeutic effectiveness by extended, controlled release into the stomach.

SUMMARY OF THE INVENTION

It has now been discovered that drugs that are highly soluble in water can be administered orally in a manner that will prolong their delivery time to spread their release rate more evenly throughout the duration of the fed mode and beyond or not as desired. This significantly reduces, and often avoids, the problems of transient overdosing caused by the initial spike in concentration entering the blood stream immediately after administration and the subsequent underdosing, and instead controls the dosage to safer and more effective levels over an extended period of time.

It has further been discovered that for drugs of high, intermediate or low solubility, the problems arising from the release of the drugs in the lower GI tract, i.e., from the failure to absorb these drugs into the blood stream prior to reaching the lower GI tract, can be mitigated as well. For all drugs regardless of solubility, therefore, this invention corrects problems such as the overgrowth of detrimental intestinal flora by drugs that are toxic to normal intestinal flora, protection of undelivered acid-labile drugs in the dosage form, chemical degradation of drugs by intestinal enzymes, loss of bioavailability of the drugs due to their leaving the acidic environment of the stomach, and chemical degradation of the drugs due to the alkaline environment of the intestinal tract. By mitigating these problems, this invention thus further improves the efficiency of the use of these drugs.

Each of the beneficial effects enumerated above is achieved by using a formulation in which the drug is dispersed in a polymeric matrix that is water-swellable rather than merely hydrophilic, that has an erosion rate that is substantially slower than its swelling rate, and that releases the drug primarily by diffusion. It has further been found that the rate of diffusion of the drug out of the matrix can be slowed by increasing the drug particle size, by the choice of polymer used in the matrix, and/or by the choice of molecular weight of the polymer. The matrix is a relatively high molecular weight polymer that swells upon ingestion, preferably to a size that is at least about twice its unswelled volume, and that promotes gastric retention during the fed mode. Upon swelling, the matrix may also convert over a prolonged period of time from a glassy polymer to a polymer that is rubbery in consistency, or from a crystalline polymer to a rubbery one. The penetrating fluid then causes release of the drug in a gradual and prolonged manner by the process of solution diffusion, i.e., dissolution of the drug in the penetrating fluid and diffusion of the dissolved drug back out of the matrix. The matrix itself is solid prior to administration and, once administered, remains undissolved in (i.e., is not eroded by) the gastric fluid for a period of time sufficient to permit the majority of the drug to be released by the solution diffusion process during the fed mode. The rate-limiting factor in the release of the drug is therefore controlled diffusion of the drug from the matrix rather than erosion, dissolving or chemical decomposition of the matrix.

For highly soluble drugs, the swelling of the polymeric matrix thus achieves two objectives—(i) the tablet swells to a size large enough to cause it to be retained in the stomach during the fed mode, and (ii) it retards the rate of diffusion of the highly soluble drug long enough to provide multi-hour, controlled delivery of the drug into the stomach. For drugs that are either sparingly soluble, of limited solubility, or of high solubility, and that experience any of the specific problems enumerated above upon reaching the lower GI tract prior to absorption into the bloodstream, the swelling of the polymeric matrix (i) renders the matrix sufficiently large to cause retention in the stomach during the fed mode, and (ii) localizes the release of the drug to the stomach and small intestine so that the drug will have its full effect without colonic degradation, inactivation, or loss of bioavailability.

In either of these aspects, the invention provides an effective means of using these drugs to treat local stomach disorders as well as a wide variety of disease conditions. For example, use of this invention provides more effective eradication of ulcer-causing bacteria in the gastric mucosa with soluble antibiotics. The invention also provides enhanced absorption of soluble drugs that are absorbed mostly in the stomach or high in the gastrointestinal tract, such as metformin hydrochloride or ciprofloxacin. The invention is also useful in providing a multi-hour flow of a drug past the upper part of the small intestine (the most efficient absorption site for many agents).

Details of these and other features of the invention will be apparent from the description that follows.

DETAILED DESCRIPTION OF THE INVENTION AND PREFERRED EMBODIMENTS

Figure 1:
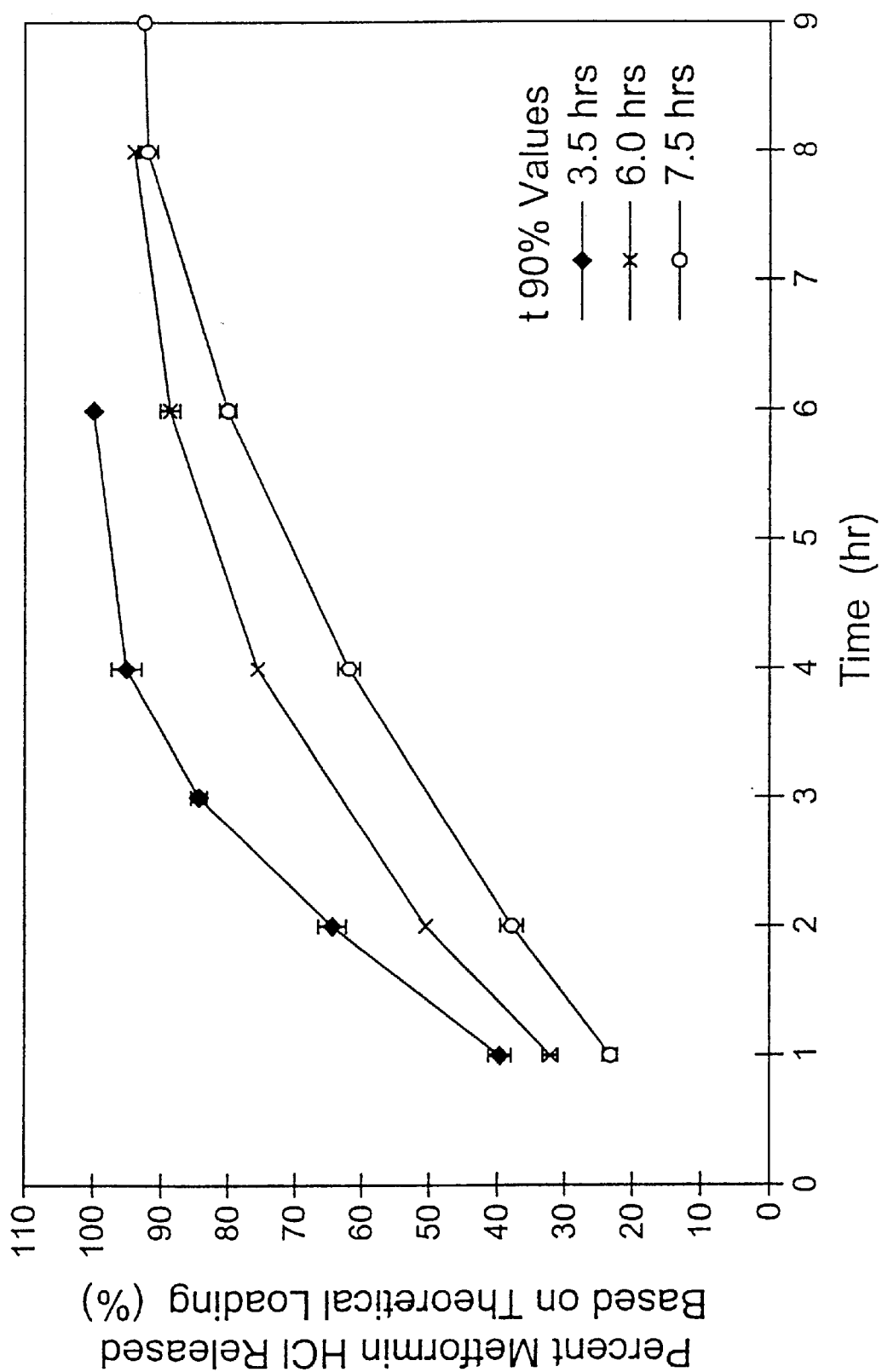
FIG. 1 is a plot showing the release rate of metformin hydrochloride from three different compositions of the drug in poly(ethylene oxide) matrices.

In aspects of this invention that are directed to highly soluble drugs, the drugs thus addressed are those that are characterized by the United States Pharmacopeia XXII as at least "freely soluble" in water, i. e., drugs whose solubility is greater than one part of the drug in about ten parts of water. Drugs of particular interest are those whose solubility is greater than one part in about five parts of water, and drugs of even greater interest are those whose solubility is greater than one part in about three parts of water. The parts referred to in this paragraph and throughout this specification are parts by weight.

The term "drug" is used herein to denote any chemical compound, complex or composition that is suitable for oral administration and that has a beneficial biological effect, preferably a therapeutic effect in the treatment of a disease or abnormal physiological condition. Examples of drugs of high solubility to which this invention is applicable are metformin hydrochloride, vancomycin hydrochloride, captopril, erythromycin lactobionate, ranitidine hydrochloride, sertraline hydrochloride, ticlopidine hydrochloride, amoxicillin, cefuroxime axetil, cefaclor, clindamycin, doxifluridine, tramadol, fluoxitine hydrochloride, ciprofloxacin, gancyclovir, bupropion, lisinopril, and esters of ampicillin. Examples of drugs of low solubility to which this invention is applicable are cefaclor, ciprofloxacin, saguinavir, ritonavir, nelfinavir, clarithromycin, azithromycin, ceftazidine, cyclosporin, digoxin, paclitaxel, iron salts, topiramate, and ketoconazole. Other drugs suitable for use and meeting the solubility criteria described above will be apparent to those skilled in the art. Drugs of particular interest are metformin hydrochloride and sertraline hydrochloride. The drug loadings (weight percent of drug relative to total of drug and polymer) in most of these cases will be about 80% or less.

The invention is also of use with drugs that have been formulated to include additives that impart a small degree of hydrophobic character, to further retard the release rate of the drug into the gastric fluid. One example of such a release rate retardant is glyceryl monostearate. Other examples are fatty acids and salts of fatty acids, one example of which is sodium myristate. The quantities of these additives when present can vary; and in most cases, the weight ratio of additive to drug will range from about 1:20 to about 1:1, and preferably from about 1:8 to about 1:2.

The water-swellable polymer forming the matrix in accordance with this invention is any polymer that is non-toxic, that swells in a dimensionally unrestricted manner upon imbibition of water, and that provides for sustained release of an incorporated drug. Examples of polymers suitable for use in this invention are cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly (2-ethyl-2-oxazoline), poly (ethyleneimine), polyurethane hydrogels, and crosslinked polyacrylic acids and their derivatives. Further examples are copolymers of the polymers listed in the preceding sentence, including block copolymers and grafted polymers. Specific examples of copolymers are PLURONIC® and TECTONIC®, which are polyethylene oxide-polypropylene oxide block copolymers available from BASF Corporation, Chemicals Div., Wyandotte, Mich., USA.

The terms "cellulose" and "cellulosic" are used herein to denote a linear polymer of anhydroglucose. Preferred cellulosic polymers are alkyl-substituted cellulosic polymers that ultimately dissolve in the gastrointestinal (GI) tract in a predictably delayed manner. Preferred alkyl-substituted cellulose derivatives are those substituted with alkyl groups of 1 to 3 carbon atoms each. Examples are methylcellulose, hydroxymethyl-cellulose, hydroxyethylcellulose, hydroxypropylcellulose, hydroxypropylmethylcellulose, and carboxymethylcellulose. In terms of their viscosities, one class of preferred alkyl-substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C. Particularly preferred alkyl-substituted celluloses are hydroxyethylcellulose and hydroxypropylmethylcellulose. A presently preferred hydroxyethylcellulose is NATRASOL® 250HX NF (National Formulary), available from Aqualon Company, Wilmington, Del., USA.

Polyalkylene oxides of greatest utility in this invention are those having the properties described above for alkyl-substituted cellulose polymers. A particularly preferred polyalkylene oxide is poly(ethylene oxide), which term is used herein to denote a linear polymer of unsubstituted ethylene oxide. Poly(ethylene oxide) polymers having molecular weights of about 4,000,000 and higher are preferred. More preferred are those with molecular weights within the range of about 4,500,000 to about 10,000,000, and even more preferred are polymers with molecular weights within the range of about 5,000,000 to about 8,000,000. Preferred poly(ethylene oxide)s are those with a weight-average molecular weight within the range of about $1 \times 10^5$ to about $1 \times 10^7$, and preferably within the range of about $9 \times 10^5$ to about $8 \times 10^6$. Poly(ethylene oxide)s are often characterized by their viscosity in solution. For purposes of this invention, a preferred viscosity range is about 50 to about 2,000,000 centipoise for a 2% aqueous solution at 20° C. Two presently preferred poly(ethylene oxide)s are POLYOX® NF, grade WSR Coagulant, molecular weight 5 million, and grade WSR 303, molecular weight 7 million, both products of Union Carbide Chemicals and Plastics Company Inc. of Danbury, Conn., USA.

Polysaccharide gums, both natural and modified (semi-synthetic) can be used. Examples are dextran, xanthan gum, gellan gum, welan gum and rhamsan gum. Xanthan gum is preferred.

Crosslinked polyacrylic acids of greatest utility are those whose properties are the same as those described above for alkyl-substituted cellulose and polyalkylene oxide polymers. Preferred crosslinked polyacrylic acids are those with a viscosity ranging from about 4,000 to about 40,000 centipoise for a 1% aqueous solution at 25° C. Three presently preferred examples are CARBOPOL® NF grades 971P, 974P and 934P (BFGoodrich Co., Specialty Polymers and Chemicals Div., Cleveland, Ohio, USA). Further examples are polymers known as WATER LOCK®, which are starch/acrylates/acrylamide copolymers available from Grain Processing Corporation, Muscatine, Iowa, USA.

The hydrophilicity and water swellability of these polymers cause the drug-containing matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. The release rate of a drug from the matrix is primarily dependent upon the rate of water imbibition and the rate at which the drug dissolves and diffuses from the swollen polymer, which in turn is related to the solubility and dissolution rate of the drug, the drug particle size and the drug concentration in the matrix. Also, because these polymers dissolve very slowly in gastric fluid, the matrix maintains its physical integrity over at least a substantial period of time, in many cases at least 90% and preferably over 100% of the dosing period. The particles will then slowly dissolve or decompose. Complete dissolution or decomposition may not occur until 24 hours or more after the intended dosing period ceases, although in most cases, complete dissolution or decomposition will occur within 10 to 24 hours after the dosing period.

The amount of polymer relative to the drug can vary, depending on the drug release rate desired and on the polymer, its molecular weight, and excipients that may be present in the formulation. The amount of polymer will be sufficient however to retain at least about 40% of the drug within the matrix one hour after ingestion (or immersion in the gastric fluid). Preferably, the amount of polymer is such that at least 50% of the drug remains in the matrix one hour after ingestion. More preferably, at least 60%, and most preferably at least 80%, of the drug remains in the matrix one hour after ingestion. In all cases, however, the drug will be substantially all released from the matrix within about ten hours, and preferably within about eight hours, after ingestion, and the polymeric matrix will remain substantially intact until all of the drug is released. The term "substantially intact" is used herein to denote a polymeric matrix in which the polymer portion substantially retains its size and shape without deterioration due to becoming solubilized in the gastric fluid or due to breakage into fragments or small particles.

The water-swellable polymers can be used individually or in combination. Certain combinations will often provide a more controlled release of the drug than their components when used individually. Examples are cellulose-based polymers combined with gums, such as hydroxyethyl cellulose or hydroxypropyl cellulose combined with xanthan gum. Another example is poly(ethylene oxide) combined with xanthan gum.

The benefits of this invention will be achieved over a wide range of drug loadings, with the weight ratio of drug to polymer ranging in general from 0.01:99.99 to about 80:20. Preferred loadings (expressed in terms of the weight percent of drug relative to total of drug and polymer) are those within the range of 15% to 80%, more preferably within the range of 30% to 80%, and most preferably in certain cases within the range of about 30% to 70%. For certain applications, however, the benefits will be obtained with drug loadings within the range of 0.01% to 80%, and preferably 15% to 80%.

The formulations of this invention may assume the form of particles, tablets, or particles retained in capsules. A preferred formulation consists of particles consolidated into a packed mass for ingestion, even though the packed mass will separate into individual particles after ingestion. Conventional methods can be used for consolidating the particles in this manner. For example, the particles can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested.

In certain embodiments of this invention, the formulation contains an additional amount of the drug applied as a quickly dissolving coating on the outside of the particle or tablet. This coating is referred to as a "loading dose" and it is included for immediate release into the recipient's bloodstream upon ingestion of the formulation without first undergoing the diffusion process that the remainder of the drug in the formulation must pass before it is released. The "loading dose" is high enough to quickly raise the blood concentration of the drug but not high enough to produce the transient overdosing that is characteristic of highly soluble drugs that are not formulated in accordance with this invention.

One presently preferred dosage form is a size 0 gelatin capsule containing either two or three pellets of drug-impregnated polymer. For two-pellet capsules, the pellets are cylindrically shaped, 6.6 or 6.7 mm (or more generally, 6.5 to 7 mm) in diameter and 9.5 or 10.25 mm (or more generally, 9 to 12 mm) in length. For three-pellet capsules, the pellets are again cylindrically shaped, 6.6 mm in diameter and 7 mm in length. For a size 00 gelatin capsule with two pellets, the pellets are cylindrical, 7.5 mm in diameter and 11.25 mm in length. For a size 00 gelatin capsule with three pellets, the pellets are cylindrical, 7.5 mm in diameter and 7.5 mm in length. Another presently preferred dosage form is a single, elongated tablet, with dimensions 18 to 22 mm in length, 6.5 to 10 mm in width, and 5 to 7.5 mm in height. Still another presently preferred dosage form is a single, elongated tablet, with dimensions 18 to 22 mm in length, 6.5 to 7.8 mm in width, and 6.2 to 7.5 mm in height. A preferred set of dimensions is 20 mm in length, 6.7 mm in width, and 6.4 mm in height. These are merely examples; the shapes and sizes can be varied considerably.

The particulate drug/polymer mixture or drug-impregnated polymer matrix can be prepared by various conventional mixing, comminution and fabrication techniques readily apparent to those skilled in the chemistry of drug formulations. Examples of such techniques are as follows:

(1) Direct compression, using appropriate punches and dies, such as those available from Elizabeth Carbide Die Company, Inc., McKeesport, Pa., USA; the punches and dies are fitted to a suitable rotary tableting press, such as the Elizabeth-Hata single-sided Hata Auto Press machine, with either 15, 18 or 22 stations, and available from Elizabeth-Hata International, Inc., North Huntington, Pa., USA;

(2) Injection or compression molding using suitable molds fitted to a compression unit, such as those available from Cincinnati Milacron, Plastics Machinery Division, Batavia, Ohio, USA.;

(3) Granulation followed by compression; and (4) Extrusion in the form of a paste, into a mold or to an extrudate to be cut into lengths.

When particles are made by direct compression, the addition of lubricants may be helpful and sometimes important to promote powder flow and to prevent capping of the particle (breaking off of a portion of the particle) when the pressure is relieved. Useful lubricants are magnesium stearate (in a concentration of from 0.25% to 3% by weight, preferably less than 1% by weight, in the powder mix), and hydrogenated vegetable oil (preferably hydrogenated and refined triglycerides of stearic and palmitic acids at about 1% to 5% by weight, most preferably about 2% by weight. Additional excipients may be added to enhance powder flowability and reduce adherence.

The term "dosage form" denotes any form of the formulation that contains an amount sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular drug, including both its pharmacological characteristics and its physical characteristics such as solubility, and with the characteristics of the swellable matrix such as its permeability, and the relative amounts of the drug and polymer. In most cases, the dosage form will be such that effective results will be achieved with administration no more frequently than once every eight hours or more, preferably once every twelve hours or more, and even more preferably once every twenty-four hours or more.

As indicated above, the dosage forms of the present invention find their greatest utility when administered to a subject who is in the digestive state (also referred to as the postprandial or "fed" mode). The postprandial mode is distinguishable from the interdigestive (or "fasting") mode by their distinct patterns of gastroduodenal motor activity, which determine the gastric retention or gastric transit time of the stomach contents.

In the interdigestive mode, the fasted stomach exhibits a cyclic activity called the interdigestive migrating motor complex (IMMC). The cyclic activity occurs in four phases:

Phase I is the most quiescent, lasts 45 to 60 minutes, and develops few or no contractions.

Phase II is marked by the incidence of irregular intermittent sweeping contractions that gradually increase in magnitude.

Phase III, which lasts 5 to 15 minutes, is marked by the appearance of intense bursts of peristaltic waves involving both the stomach and the small bowel.

Phase IV is a transition period of decreasing activity which lasts until the next cycle begins.

The total cycle time is approximately 90 minutes, and thus, powerful peristaltic waves sweep out the contents of the stomach every 90 minutes during the interdigestive mode. The IMMC may function as an intestinal housekeeper, sweeping swallowed saliva, gastric secretions, and debris to the small intestine and colon, preparing the upper tract for the next meal while preventing bacterial overgrowth. Pancreatic exocrine secretion of pancreatic peptide and motilin also cycle in synchrony with these motor patterns.

The postprandial or fed mode is induced by food ingestion, and begins with a rapid and profound change in the motor pattern of the upper GI tract, the change occurring over a period of 30 seconds to one minute. The stomach generates 3–4 continuous and regular contractions per minute, similar to those of the interdigestive mode but of about half the amplitude. The change occurs almost simultaneously at all sites of the GI tract, before the stomach contents have reached the distal small intestine. Liquids and small particles flow continuously from the stomach into the intestine. Contractions of the stomach result in a sieving process that allows liquids and small particles to pass through a partially open pylorus. Indigestible particles greater than the size of the pylorus are retropelled and retained in the stomach. Particles exceeding about 1 cm in size are thus retained in the stomach for approximately 4 to 6 hours. The dosage form of the present invention is designed to achieve the minimal size through swelling following ingestion during the fed mode.

The following examples are offered for purposes of illustration, and are not intended to limit the invention in any manner.

EXAMPLE 1

This example illustrates the controlled-release behavior of metformin hydrochloride, a highly soluble drug (whose solubility is approximately 30%), from a polymeric matrix consisting of poly(ethylene oxide). Three different dose levels were prepared—systems designed to release 90% of their drug contents at approximately 3 hours, 6 hours, and 8 hours, respectively.

Drug and polymer, with 0.5% magnesium stearate as a tableting lubricant, were compressed into pellets measuring 7.2 mm diameter×8.8 mm length and weighing 390 mg for samples designed for 3-hour and 6-hour release, and 7.4 mm diameter×8.5 mm length and weighing 380 mg for samples designed for 8-hour release, and two pellets of a given type were incorporated into a single gelatin capsule. Thus, three different types of gelatin capsule were prepared as follows:

| $t_{90\%} \cong 3$ hours | |
|---|---|
| metformin hydrochloride | 250.00 mg |
| POLYOX ® 1105, molecular weight 900,000 | 138.67 |
| magnesium stearate | 1.95 |
| Total | 390.62 mg |
| $t_{90\%} \cong 6$ hours | |
| metformin hydrochloride | 250.00 mg |
| POLYOX ® Coagulant, molecular weight 5,000,000 | 138.67 |
| magnesium stearate | 1.95 |
| Total | 390.62 mg |
| $t_{90\%} \cong 8$ hours | |
| metformin hydrochloride | 125.00 mg |
| POLYOX ® 303, molecular weight 7,000,000 | 266.11 |
| magnesium stearate | 1.97 |
| Total | 393.08 mg |

Release rate tests on each of these three formulations were performed in modified artificial gastric fluid by the following procedure.

Dissolution was performed in a USP Apparatus 2, modified to include a stainless steel cone (⅞ inch in height and ⅞ inch in diameter at the base) at the bottom of each vessel, placed directly beneath the paddle shaft to eliminate the "dead zone" effect. A paddle speed of 60 rpm and a bath temperature of 37.4° C. were used. The gelatin capsule was opened and the individual pellets and empty gelatin capsule were dropped into the dissolution vessel containing 900 mL of modified simulated gastric fluid (7 mL of hydrochloric acid and 2 g of sodium chloride in 100 mL of deionized water; the enzyme pepsin was omitted). Once the pellets had settled to the bottom of the vessel, the paddle rotation was initiated. Samples 5 mL in size were taken at specified time points, and the sample volumes were not replaced. The samples were diluted as necessary for quantitative analysis by HPLC.

The results are shown in FIG. 1, where the filled diamonds represent the $t_{90\%} \cong 3$ formulation, the x's represent the $t_{90\%} \cong 6$ formulation, and the open circles represent the $t_{90\%} \cong 8$ formulation. The curves show that the $t_{90\%}$ value of the first formulation was fairly close to 3.5 hours, the $t_{90\%}$ value of the second formulation was fairly close to 6.0 hours, and $t_{90\%}$ value of the third formulation was fairly close to 7.5 hours.

EXAMPLE 2

This example illustrates the controlled-release behavior of captopril from a polymeric matrix consisting of poly (ethylene oxide), both with and without glyceryl monostearate (8% by weight). The formulations used were as follows:

| | |
|---|---|
| 1. Captopril | 92.50 mg |
| Poly(ethylene oxide) (POLYOX ® 301), molecular weight 4,000,000 | 407.50 |
| Total | 500.00 mg |
| 2. Captopril | 92.5 mg |
| glyceryl monostearate | 15.0 |
| Poly(ethylene oxide) (POLYOX ® 301), molecular weight 4,000,000 | 392.5 |
| Total | 500.0 mg |

Each formulation was compressed into a tablet measuring 6.0 mm diameter×6.7 mm length and weighing 180 mg. Release rate tests on each of the two tablets were performed in modified simulated gastric fluid by the procedure of Example 1, except that the paddle rotation speed was 30 rpm and the tablets were dropped directly into the dissolution vessel.

Figure 2:
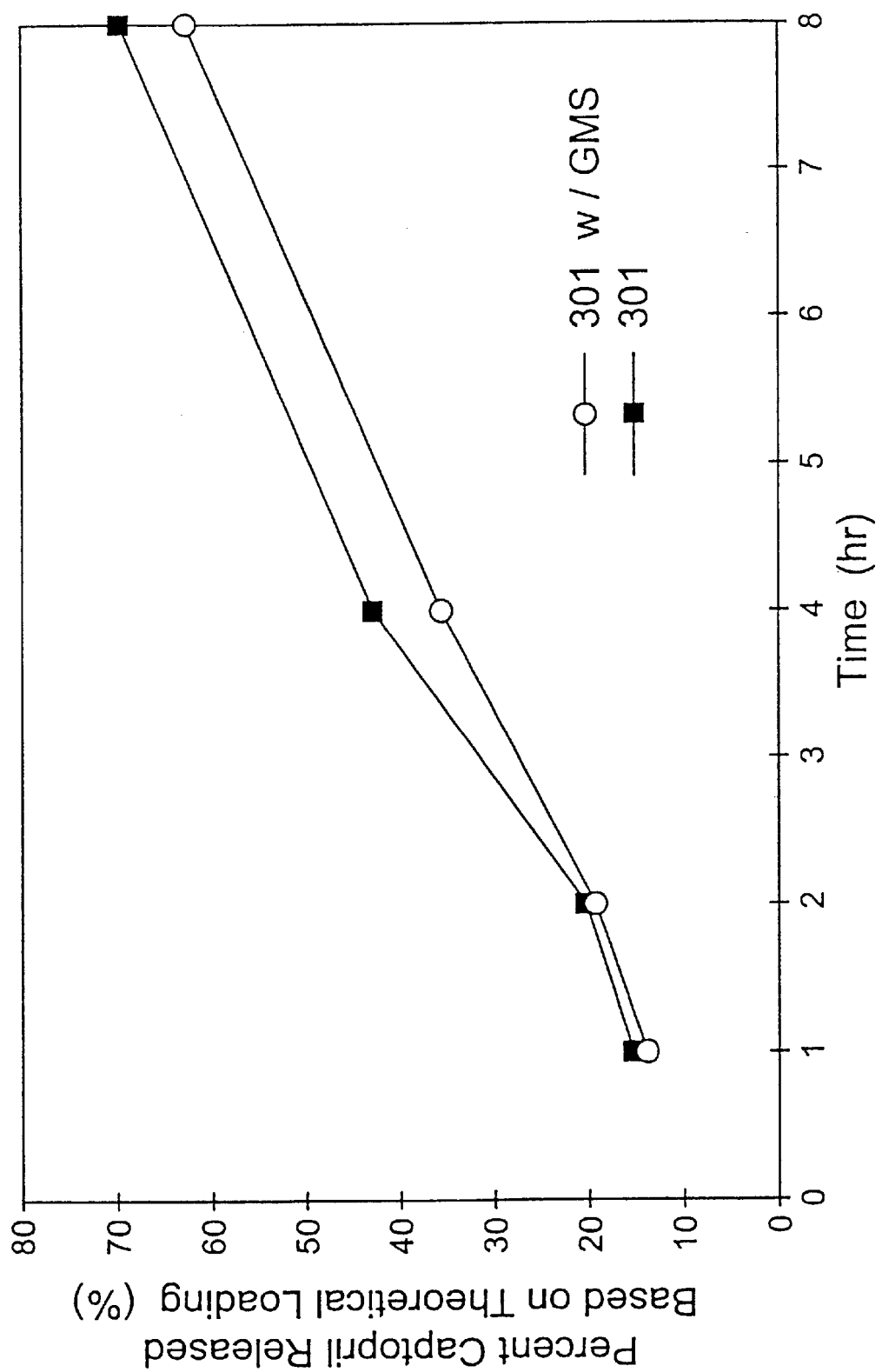
FIG. 2 is a plot showing the release rate of captopril from a poly(ethylene oxide) matrix, in accordance with this invention, both with and without glyceryl monostearate as a solubility modifier.

The results are shown in FIG. 2, where the filled squares represent Formulation No. 1 consisting of captopril and poly(ethylene oxide) only, and the open circles represent Formulation No. 2 which further contained glyceryl monostearate.

EXAMPLE 3

This example illustrates the controlled-release behavior of captopril from a polymeric matrix of hydroxyethyl cellulose with the inclusion of glyceryl monostearate, but at varying pellet sizes. The formulation contained 19% captopril (all percents by weight) and 4.8% glyceryl monostearate in hydroxyethyl cellulose of molecular weight within the range of 1,000,000 to 1,500,000. The pellet sizes and weights were (a) 3.3 mm diameter×3.5 mm length at 35 mg (referred to herein as 3-mm tablets), (b) 4.3 mm diameter×4.9 mm length at 75 mg (referred to herein as 4-mm tablets), and (c) 6.3 mm diameter×6.5 mm length at 187 mg (referred to herein as 6-mm tablets).

Figure 3:
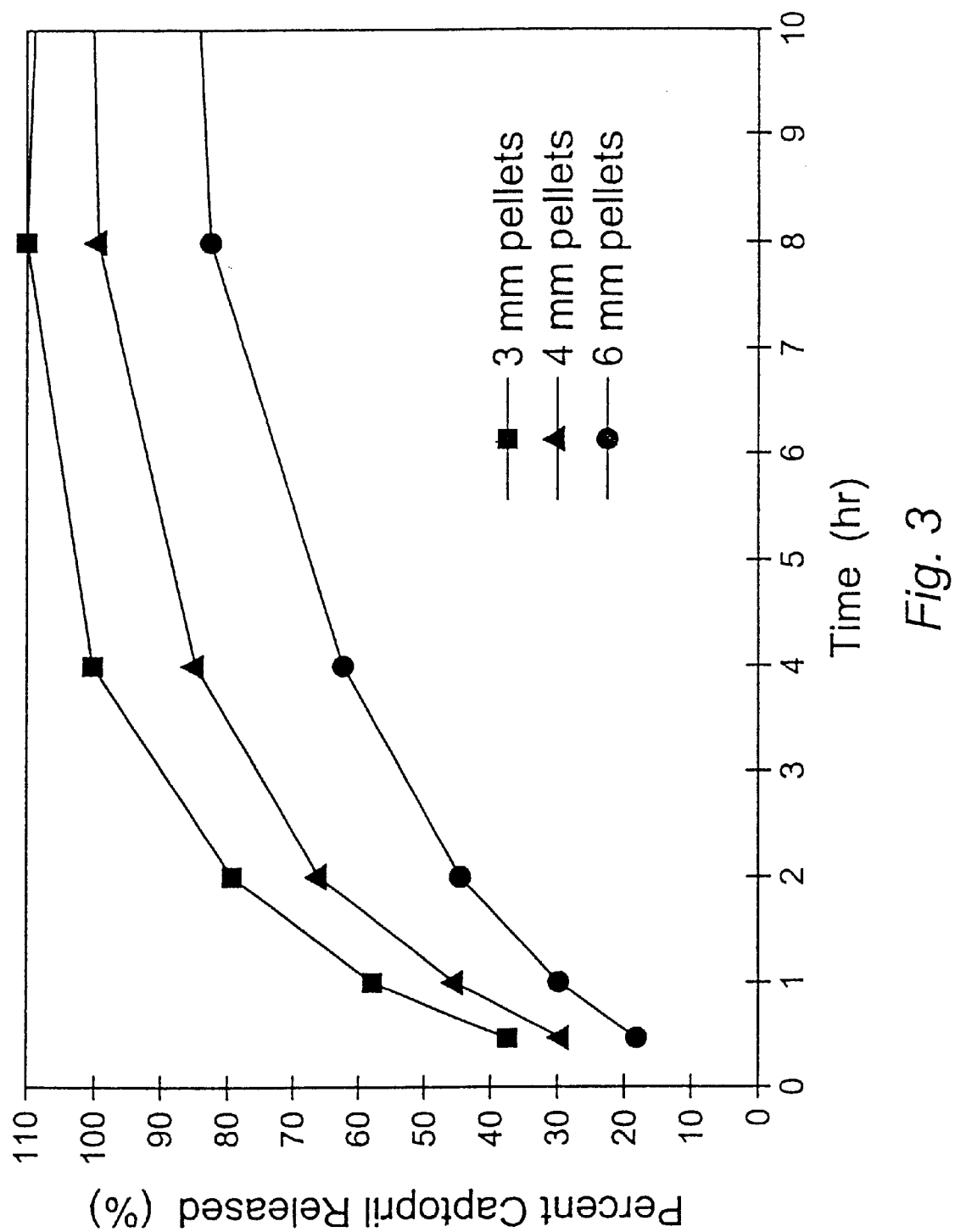
FIG. 3 is a plot showing the release rate of captopril from hydroxyethyl cellulose, in which the pellet size was varied.

Release rate tests on each of the three tablet sizes (fifteen of the 3-mm tablets, seven of the 4-mm tablets, and three of the 6-mm tablets) were performed using the procedures of Example 1, except that a weighted watchglass was used in place of the stainless steel cone, and analyses of the samples were performed by UV/Vis. The results are shown in FIG. 3, where the filled squares represent the 3-mm pellets, the filled triangles the 4-mm pellets, and the filled circles the 6-mm pellets. This demonstrates the variation of pellet size as a further means of varying the release pattern, the larger pellets having less surface area.

EXAMPLE 4

Figure 4:
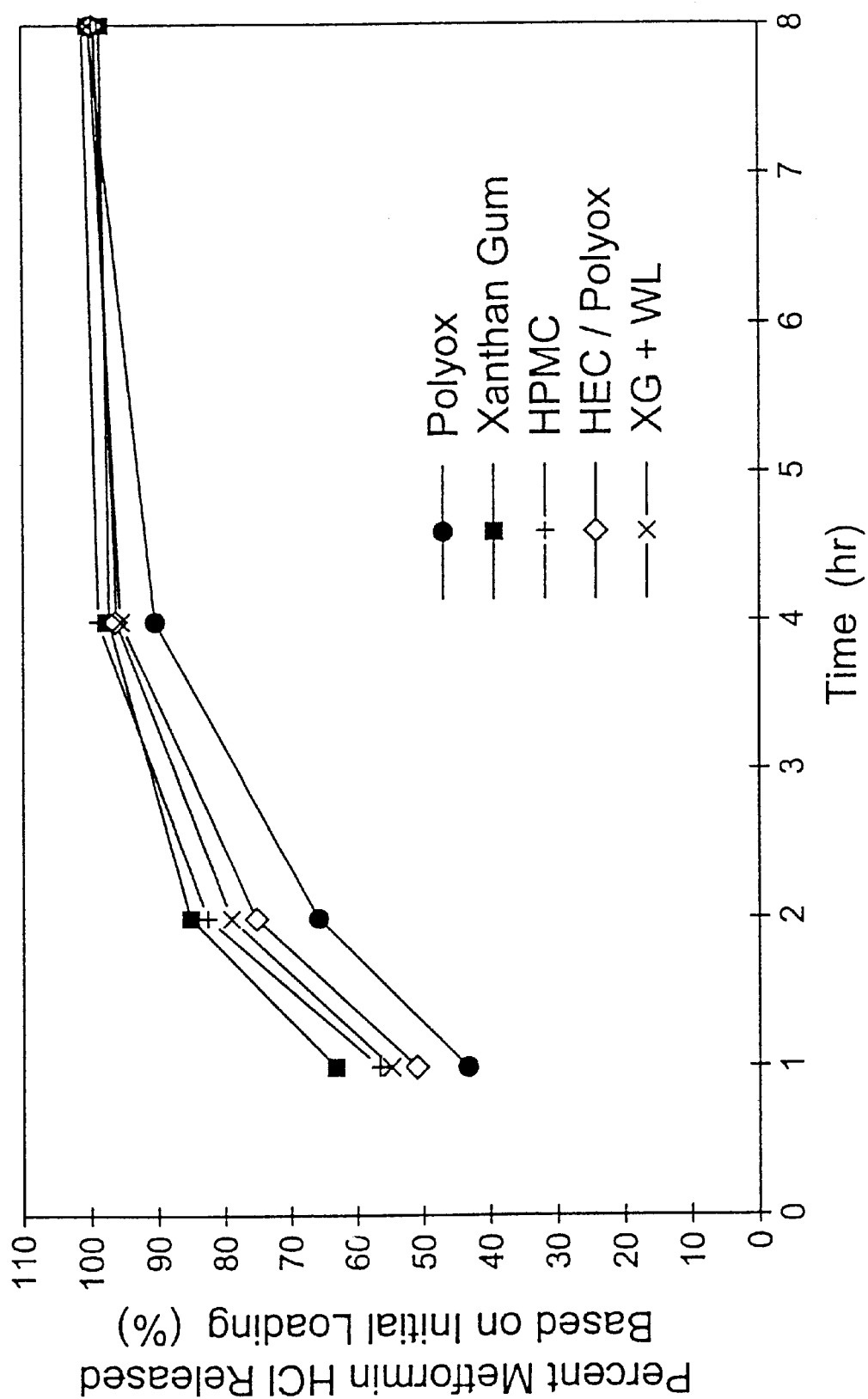
FIG. 4 is a plot showing the release rate of metformin hydrochloride from various polymeric matrices.

This example further illustrates the controlled release of metformin hydrochloride, using a higher drug loading, and various polymers and combinations of polymers. The procedures used were the same as those described above, and the formulations together with the symbols used in FIG. 4 where the results are plotted, were as follows (all percentages are by weight):

Filled circles: 79.6% metformin HCl; 20% poly(ethylene oxide) (POLYOX® 303, molecular weight 7,000,000); 0.4% magnesium stearate. Pellet dimensions 6.04 mm diameter×9.48 mm length; containing approximately 478 mg metformin HCl.

Filled squares: 79.6% metformin HCl; 20% xanthan gum (KELTROL® F, Kelco, Div. of Merck & Co., Inc., San Diego, Calif., USA); 0.4% magnesium stearate. Pellet dimensions 6.06 mm diameter×9.40 mm length; containing approximately 483 mg metformin HCl.

Plus signs: 79.6% metformin HCl; 20% hydroxypropylmethyl cellulose (BENECEL® 824, Aqualon Co., Wilmington, Del., USA), viscosity (2%, 20° C.) 11,000 to 15,000 cps; 0.4% magnesium stearate. Pellet dimensions 6.06 mm diameter×9.49 mm length; containing approximately 480 mg metformin HCl.

Open diamonds: 79.6% metformin HCl; 5% hydroxyethyl cellulose (250HX, molecular weight 1,000,000); 15% poly(ethylene oxide (POLYOX® 303, molecular weight 7,000,000); 0.4% magnesium stearate. Pellet dimensions 6.06 mm diameter×9.60 mm length; containing approximately 480 mg metformin HCl.

x's: 79.6% metformin HCl, 18.05% xanthan gum (KELTROL® F); 1.99% WATER LOCKS D-223 (starch graft poly(2-propenamide-co-2-propenoic acid)), mixed sodium and aluminum salts, Grain Processing Corporation, Muscatine, Iowa, USA); 0.4% magnesium stearate. Pellet dimensions were 6.06 mm diameter×9.24 mm length; containing approximately 476 mg metformin HCl total.

EXAMPLE 5

Figure 5:
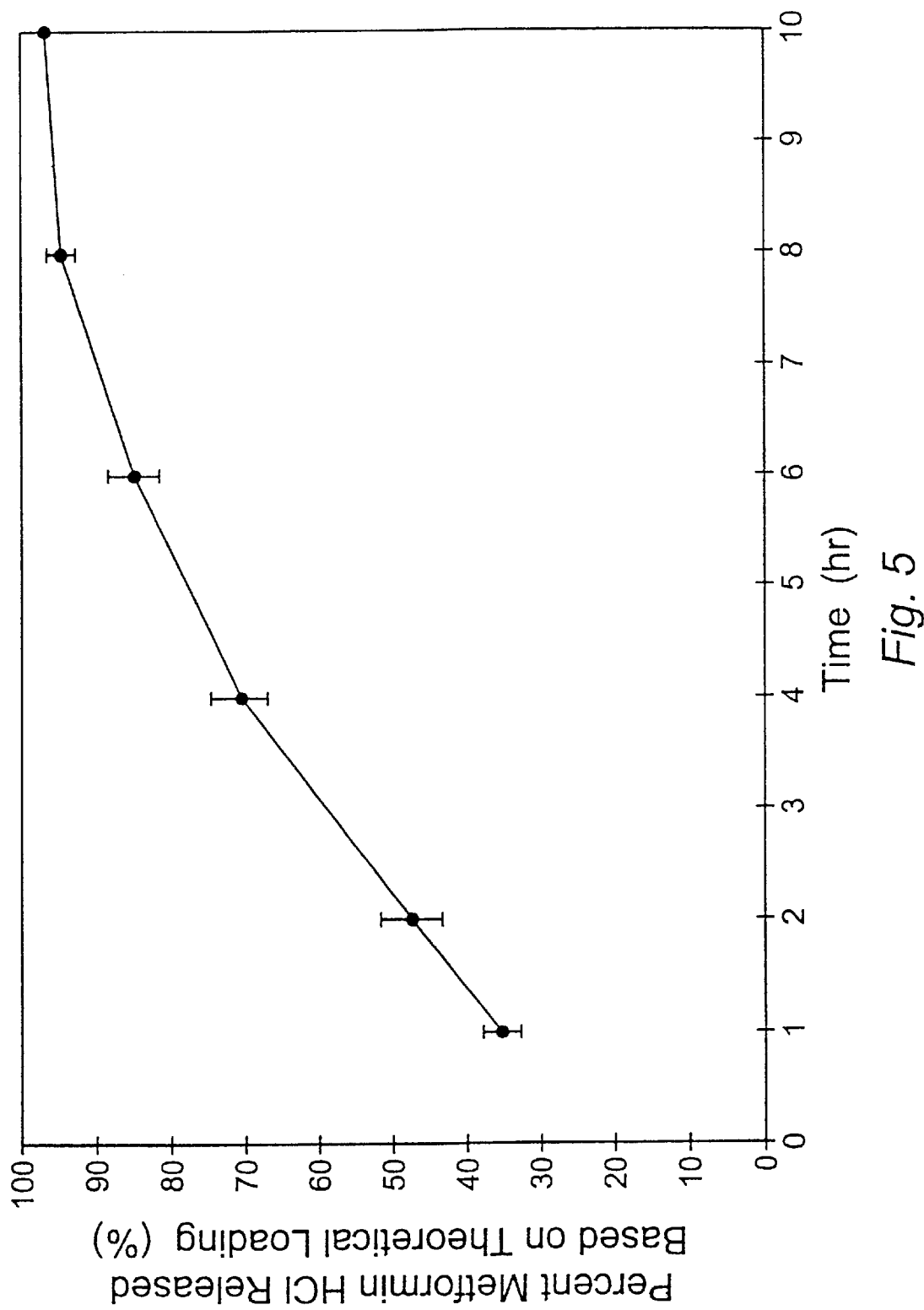
FIG. 5 is a plot showing the release rate of metformin hydrochloride from a single capsule-shaped tablet.

This example further illustrates the controlled release of metformin hydrochloride from a single capsule-shaped tablet. The procedures used were the same as those described above, and the resulting curve is plotted in FIG. 5. The formulation was as follows (all percentages are by weight): 64% metformin HCl; 35.5% poly(ethylene oxide) (POLYOX® 303, molecular weight 7,000,000); 0.5% magnesium stearate; plus an additional 2% OPADRY® Clear coating (hydroxypropyl methylcellulose, Colorcon, West Point, Pa., USA). The tablet dimensions were 6.48 mm diameter×7.20 mm height×19.21 mm length, and contained approximately 506 mg metformin HCl per tablet.

EXAMPLE 6

Figure 6:
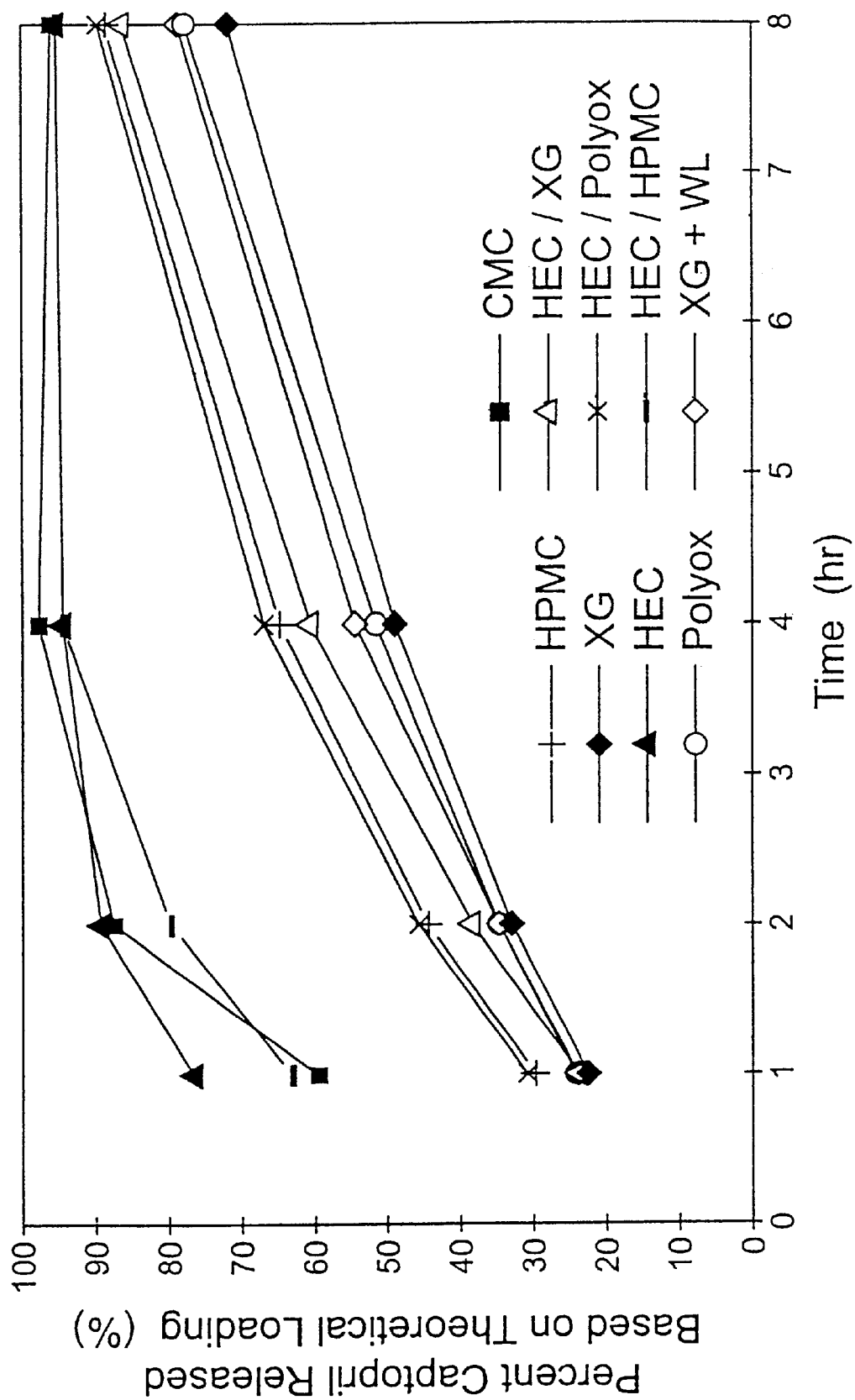
FIG. 6 is a plot showing the release rate of captopril from various polymeric matrices.

This example further illustrates the controlled release of captopril, using various polymers and combinations of polymers. The procedures used were the same as those described above, and the formulations together with the symbols used in FIG. 6 where the results are plotted, were as follows (all percentages are by weight):

Plus signs: 80% captopril; 20% hydroxypropylmethyl cellulose (BENECEL® 824, viscosity (2%, 20° C.) 11,000 to 15,000 cps). Pellet dimensions: 6.03 mm diameter×9.25 mm length, 2 pellets weighing 293 mg each, containing approximately 469 mg captopril total.

Filled diamonds: 80% captopril; 20% xanthan gum (KELTROL® F). Pellet dimensions: 6.04 mm diameter×9.18 mm length, 2 pellets weighing 299 mg each, containing approximately 478 mg captopril total.

Filled triangles: 80% captopril; 20% hydroxyethyl cellulose (250HX, molecular weight 1,000,000). Pellet dimensions: 6.03 mm diameter×9.53 mm length, 2 pellets weighing 299 mg each, containing approximately 478 mg captopril total.

Open circles: 80% captopril; 20% poly(ethylene oxide) (POLYOX® 303, molecular weight 7,000,000). Pellet dimensions: 6.04 mm diameter×9.59 mm length, 2 pellets weighing 301 mg each, containing approximately 482 mg captopril total.

Filled squares: 80% captopril; 20% carboxymethyl cellulose (12M31P, molecular weight 250,000). Pellet dimensions: 6.04 mm diameter×9.18 mm length, 2 pellets weighing 299 mg each, containing approximately 478 mg captopril total.

Open triangles: 79.93% captopril; 10.03% hydroxyethyl cellulose (250HX, molecular weight 1,000,000); 10.04% xanthan gum (KELTROL® F). Pellet dimensions: 6.04 mm diameter×9.26 mm length, 2 pellets weighing 296 mg each, containing approximately 473 mg captopril total.

x's: 79.96% captopril; 10.03% hydroxyethyl cellulose (250HX, molecular weight 1,000,000); 10.01% poly(ethylene oxide) (POLYOX® 303, molecular weight 7,000,000). Pellet dimensions: 6.04 mm diameter×9.41 mm length, 2 pellets weighing 297 mg each, containing approximately 475 mg captopril total.

Dashes: 80% captopril; 10% hydroxyethyl cellulose (250HX, molecular weight 1,000,000); 10% hydroxypropylmethyl cellulose (BENECEL® 824, viscosity (2%, 20° C.) 11,000 to 15,000 cps). Pellet dimensions: 6.04 mm diameter×9.41 mm length, 2 pellets weighing 298 mg each, containing approximately 477 mg captopril total.

Open diamonds: 79.96% captopril; 18.05% xanthan gum (KELTROL® F); 1.99% WATERLOCK® D-223. Pellet dimensions: 6.04 mm diameter×9.16 mm length, 2 pellets weighing 297 mg each, containing approximately 475 mg captopril total.

EXAMPLE 7

Figure 7:
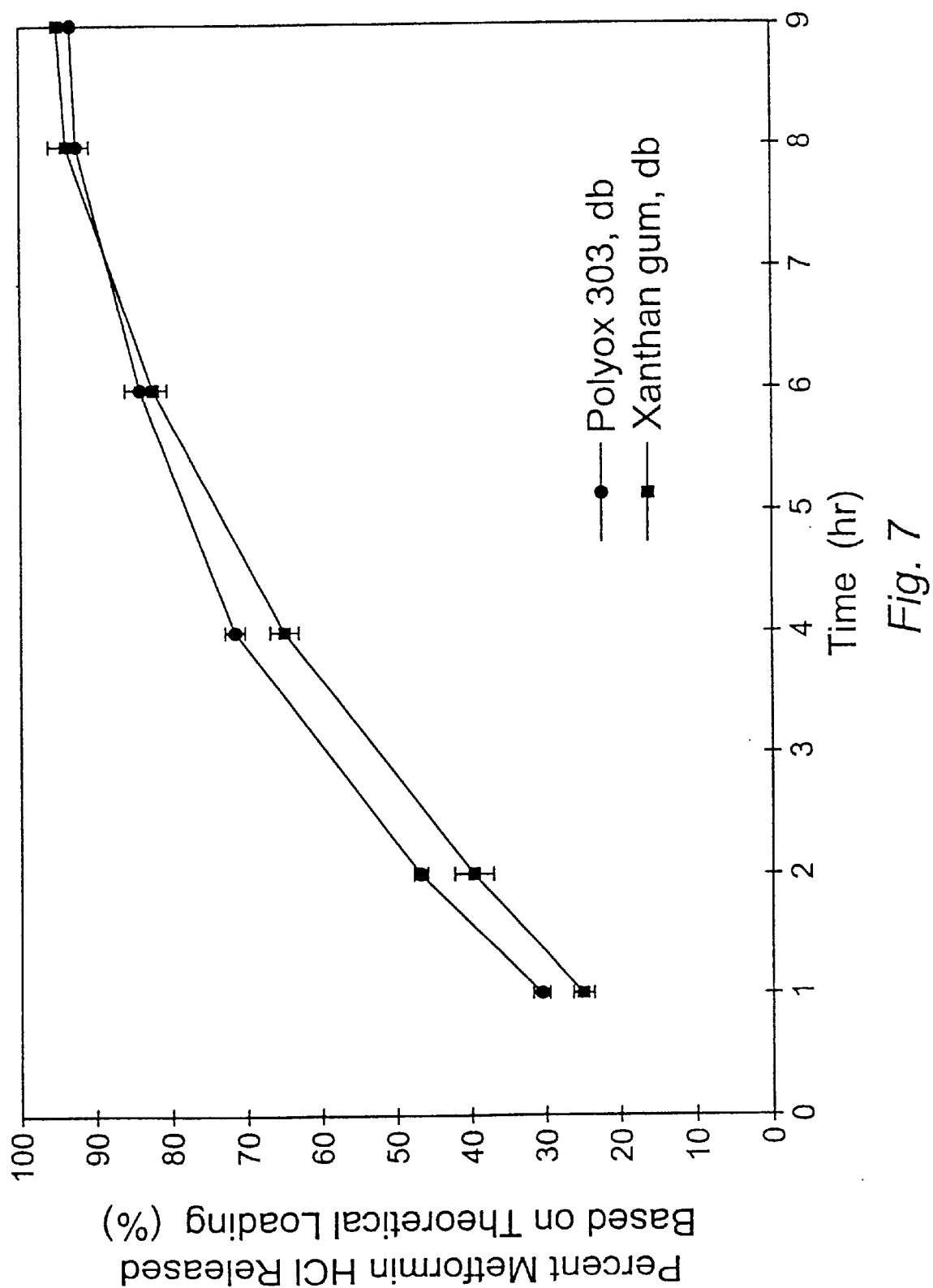
FIG. 7 is a plot showing further release rate studies of metformin hydrochloride from two different polymeric matrices.

This example presents further data on metformin hydrochloride formulations, illustrating the effect of lower drug loadings than those used in the preceding examples. The procedures used were the same as those described above, and the formulations together with the symbols used in FIG. 7 where the results are plotted, were as follows (all percentages are by weight):

Filled squares: 32.5% metformin HCl; 67% poly(ethylene oxide) (POLYOX® 303, molecular weight 7,000,000); 0.5% magnesium stearate. Pellet dimensions 6.62 mm diameter×10.40 mm length, 2 pellets weighing 400 mg each, containing approximately 260 mg metformin HCl total.

Open circles: 32.5% metformin HCl; 67% xanthan gum (KELTROL® F); 0.5% magnesium stearate. Pellet dimensions 6.65 mm diameter×9.28 mm length; 2 pellets weighing 401 mg each, containing approximately 261 mg metformin HCl total.

EXAMPLE 8

Figure 8:
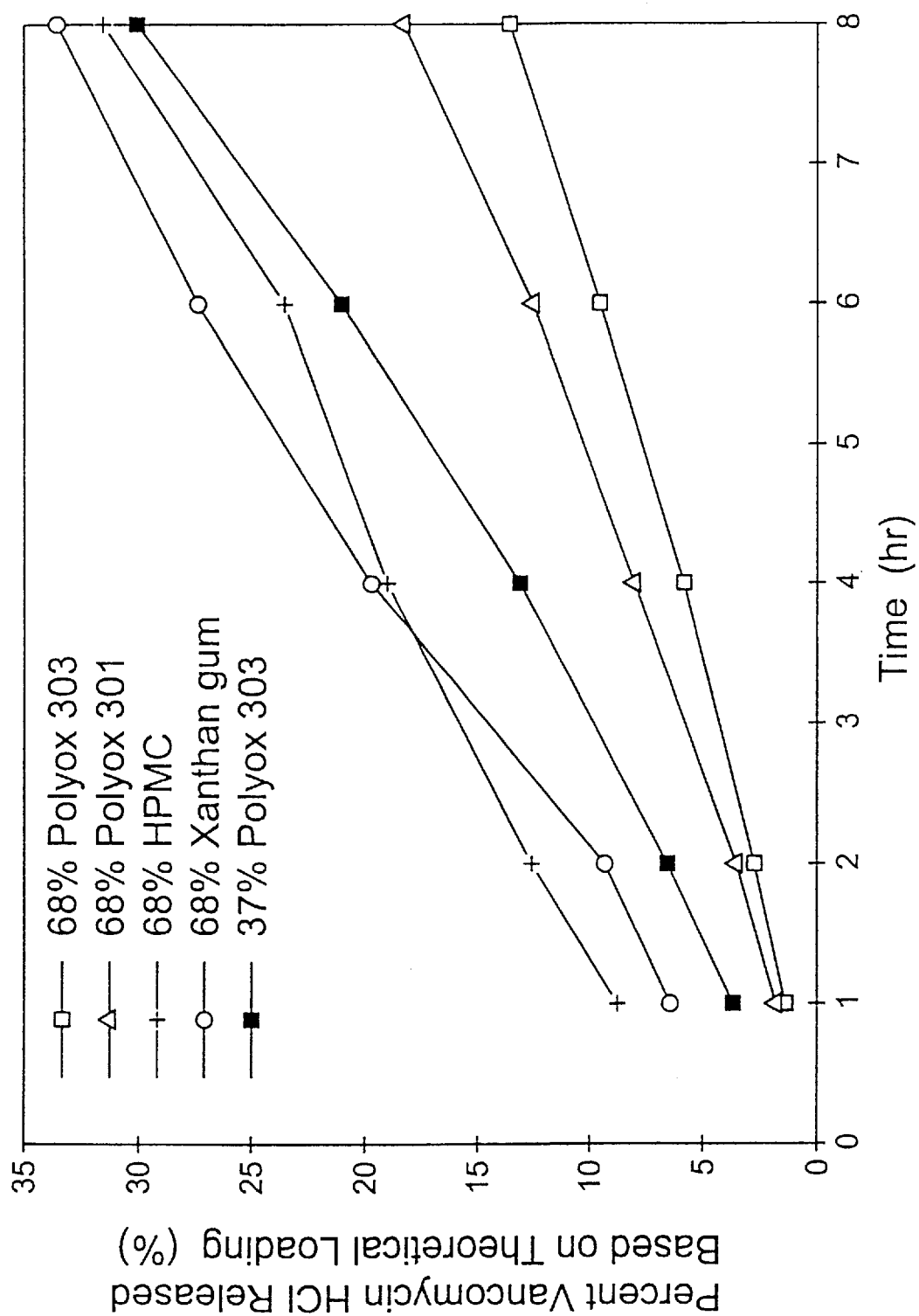
FIG. 8 is a plot showing the release rate of vancomycin hydrochloride from different polymeric matrices.

This example illustrates the sustained release of vancomycin hydrochloride from various polymers. The procedures used were the same as those described above, and the formulations together with the symbols used in FIG. 8 where the results are plotted, were as follows (all percentages are by weight):

Open squares: 31.5% vancomycin hydrochloride; 68% poly(ethylene oxide) (POLYOX® 303, molecular weight 7,000,000); 0.5% magnesium stearate. Pellet dimensions: 6.59 mm diameter×10.23 mm length, 2 pellets weighing 403 mg each, containing approximately 254 mg vancomycin hydrochloride total.

Open triangles: 31.5% vancomycin hydrochloride; 68% poly(ethylene oxide) (POLYOX® 301, molecular weight 4,000,000); 0.5% magnesium stearate. Pellet dimensions: 6.59 mm diameter×10.28 mm length, 2 pellets weighing 402 mg each, containing approximately 253 mg vancomycin hydrochloride total.

x's: 31.5% vancomycin hydrochloride; 68% hydroxypropyl methylcellulose (BENECEL® 824, viscosity 11,000–15,000 cps (2% solution at 20° C.)); 0.5% magnesium stearate. Pellet dimensions: 6.59 mm diameter×10.10 mm length, 2 pellets weighing 405 mg each, containing approximately 255 mg vancomycin hydrochloride total.

Open circles: 31.5% vancomycin hydrochloride; 68% xanthan gum (KELTROL® F); 0.5% magnesium stearate. Pellet dimensions: 6.62 mm diameter×9.77 mm length, 2 pellets weighing 401 mg each, containing approximately 253 mg vancomycin hydrochloride total.

Filled squares: 62.5% vancomycin hydrochloride; 37% poly(ethylene oxide) (POLYOX® 303, molecular weight 7,000,000); 0.5% magnesium stearate. Pellet dimensions: 6.60 mm diameter×10.01 mm length, 2 pellets weighing 409 mg each, containing approximately 511 mg vancomycin hydrochloride total.

In the prior art, vancomycin and its salts are administered by injection, due to poor absorption when administered orally. By providing for all or at least a portion of the total administered amount to be delivered by controlled delivery in the gastric retentive system of this invention, that portion so delivered is directed to the proximal portion of the small intestine, the most efficient site for absorption of this drug, resulting in an enhanced absorption from the oral dosage form of the invention.

EXAMPLE 9

This example illustrates the difference between subjects in the fed mode and subjects not in the fed mode in terms of the gastric retention of tablets of various sizes administered orally. Both Beagle dogs and human subjects were used.

Barium-containing tablets for oral administration were prepared from the following ingredients:

25% Barium Sulfate
30% PolyOx 303 (average molecular weight 7,000,000)
44.5% Hydroxypropylcellulose
0.5% Magnesium Stearate For tests on Beagle dogs, 400-mg tablets measuring 5.8 mm diameter×5.1 mm height×15.4 mm length were prepared in a tablet press at 2,500 psi pressure, and 800-mg tablets measuring 7.9 mm diameter×5.6 mm height×19.1 mm length were prepared in a tablet press at 5,000 psi. Four beagle dogs were used, and the location of the tablets in the GI tract was followed using fluoroscopy. Two studies were initiated with the dogs. In the first study, each dog received two tablets (one 400-mg and one 800-mg) with a small amount of water after a 16-hour fast. In the second study, each dog received two tablets (one 400-mg and one 800-mg) thirty minutes after ingesting 50 grams of a standard meal. The location of the tablets (in or out of the stomach) was monitored every 30 minutes with the fluoroscope.

The fluoroscopy revealed that tablets that were administered while the dogs were in the fasted condition were emptied from the dogs' stomachs within 90 minutes: in two of the dogs, the stomachs contained no barium tablets at 30 minutes, in a third this was true at 60 minutes, and in the fourth at 90 minutes. Tablets that were administered while the dogs were in the fed state remained in the dogs' stomach for between 4 and 5 hours.

Human tests were performed on ten normal adults of both sexes, each taking part in two trials, the first after fasting and the second after a bacon and egg breakfast of approximately 1,500 calories. The tablets used in the tests had the same composition as those used for the Beagle dogs and measured either 4 mm×4 mm or 6 mm×6 mm. The subjects were X-rayed at 30 minutes and at 1, 2, 4, 6, 8, 10, and approximately 12 hours after ingesting the tablets. In some subjects, visualization was achieved by ultrasound rather than X-rays.

Imaging revealed that in the fasted trials, the tablets left the stomach in 30 minutes to one hour after administration. In the fed trials, the tablets demonstrated multiple-hour retention in the stomach in all subjects, 80% of the contents of all tablets being retained at 4 hours. Five of the ten subjects retained the tablets for 6 hours or more, and four of these five retained them for ten hours or more.

EXAMPLE 10

Figure 9:
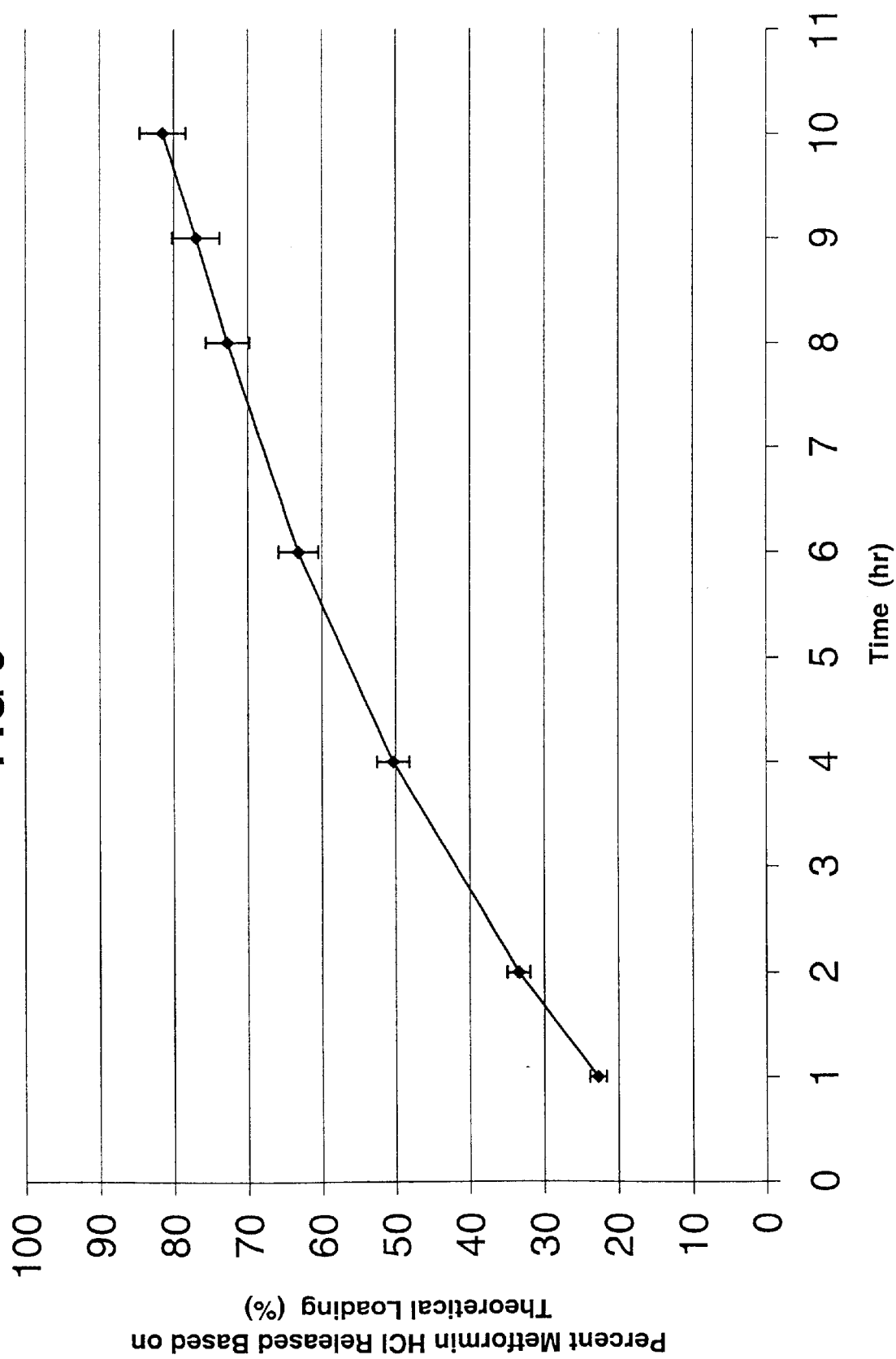
FIG. 9 is a plot showing the release rate of metformin hydrochloride from a single capsule-shaped tablet.

This example further illustrates the controlled release of metformin hydrochloride from a single capsule-shaped tablet. The procedures used were the same as those described above, and the resulting curve is plotted in FIG. 9. The formulation was as follows (all percentages are by weight): 48.5% metformin HCl; 49% poly(ethylene oxide) (POLYOX® 303, molecular weight 7,000,000); 0.5% magnesium stearate; plus an additional 2% OPADRY® Clear coating (hydroxypropyl methylcellulose, Colorcon, West Point, Pa., USA). The tablet dimensions were 9.66 mm diameter×6.95 mm height×19.24 mm length, and contained approximately 506 mg metformin HCl per tablet.

The foregoing is offered primarily for purposes of illustration. It will be readily apparent to those skilled in the art that the components, additives, proportions, methods of formulation, and other parameters of the invention can be modified further or substituted in various ways without departing from the spirit and scope of the invention.

What is claimed is:

1. A controlled-release oral drug dosage form for releasing a drug whose solubility in water is greater than one part by weight of said drug in ten parts by weight of water, said dosage form comprising a solid polymeric matrix with said drug dispersed therein at a weight ratio of drug to polymer of from about 15:85 to about 80:20, said polymeric matrix being one that swells upon imbibition of water thereby attaining a size large enough to promote retention in the stomach during said fed mode, that releases said drug into gastric fluid by the dissolution and diffusion of said drug out of said matrix by said gastric fluid, that upon immersion in gastric fluid retains at least about 40% of said drug one hour after such immersion and releases substantially all of said drug within about eight hours after such immersion, and that remains substantially intact until all of said drug is released.

2. A dosage form of claim 1 in which the solubility of said drug in water is greater than one part by weight of said drug in five parts by weight of water.

3. A dosage form of claim 1 in which said drug is a member selected from the group consisting of metformin hydrochloride, vancomycin hydrochloride, captopril, erythromycin lactobionate, ranitidine hydrochloride, sertraline hydrochloride, tramadol and ticlopidine hydrochloride.

4. A dosage form of claim 1 in which said drug is metformin hydrochloride.

5. A dosage form of claim 1 in which said drug is sertraline hydrochloride.

6. A dosage form of claim 1 in which said drug is captopril.

7. A dosage form of claim 1 in which said drug is vancomycin hydrochloride.

8. A dosage form of claim 1 in which said polymeric matrix is formed of a polymer selected from the group consisting of poly(ethylene oxide), cellulose, alkyl-substituted celluloses, crosslinked polyacrylic acids, and xanthan gum.

9. A dosage form of claim 8 in which said alkyl-substituted celluloses are members selected from the group consisting of hydroxymethyl-cellulose, hydroxyethyl-cellulose, hydroxypropyl-cellulose, hydroxypropylmethyl-cellulose, and carboxymethyl-cellulose.

10. A dosage form of claim 1 in which said polymeric matrix is formed of poly(ethylene oxide) at a molecular weight of at least about 4,000,000.

11. A dosage form of claim 1 in which said polymeric matrix is formed of poly(ethylene oxide) at a molecular weight in the range of about 4,500,000 to about 10,000,000.

12. A dosage form of claim 1 in which said polymeric matrix is formed of poly(ethylene oxide) at a molecular weight in the range of about 5,000,000 to about 8,000,000.

13. A dosage form of claim 1 in which said polymeric matrix upon immersion in gastric fluid retains at least about 50% of said drug one hour after such immersion.

14. A dosage form of claim 1 in which said polymeric matrix upon immersion in gastric fluid retains at least about 60% of said drug one hour after such immersion.

15. A dosage form of claim 1 in which said polymeric matrix upon immersion in gastric fluid retains at least about 80% of said drug one hour after such immersion.

16. A dosage form of claim 1 further comprising a member selected from the group consisting of glyceryl monostearate and sodium myristate, formulated with said drug to further retard the release of said drug to said gastric fluid.

17. A dosage form of claim 1 in which said polymeric matrix consists of two cylindrical tablets, each measuring about 9 mm to about 12 mm in length and about 6.5 mm to about 7 mm in diameter.

18. A dosage form of claim 1 in which said polymeric matrix consists of a single elongated tablet measuring about 18 mm to about 22 mm in length, about 6.5 mm to about 7.8 mm in width, and about 6.2 to 7.5 mm in height.

19. A method of administering to a subject a drug that is therapeutic to said subject when absorbed in the stomach and doing so in a manner that substantially avoids the alteration of intestinal flora that said drug otherwise tends to cause, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach and substantially avoiding contact of said drug with said intestinal flora.

20. A method in accordance with claim 19 in which said drug is a member selected from the group consisting of amoxicillin, cefuroxime axetil, cefaclor, clindamycin, clarithromycin, azithromycin, ceftazidine, and ciprofloxacin.

21. A method in accordance with claim 19 in which said drug is a highly soluble drug selected from the group consisting of amoxicillin, cefuroxime axetil, cefaclor, and clindamycin.

22. A method of treating a subject suffering from infections selected from the group consisting of pneumonia, sinus bacterial infections, topical bacterial infections and staphylococcus infections, by administering to said subject a drug which is a member selected from the group consisting of amoxicillin, cefuroxime axetil, cefaclor, clindamycin, clarithromycin, azithromycin, and ceftazidine, without substantially causing side effects resulting from the alteration of the intestinal flora of said subject, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach and substantially avoiding contact of said drug with said intestinal flora.

23. A method in accordance with claim 22 in which said drug is a highly soluble drug selected from the group consisting of amoxicillin, cefuroxime axetil, cefaclor, and clindamycin.

24. A method of administering to a subject a drug that is therapeutic to said subject when absorbed in the stomach but also degradable by colonic bacterial enzymes residing in lower gastrointestinal tract enterocytes, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach and substantially avoiding contact of said drug with said intestinal enzymes and said drug transporters.

25. A method in accordance with claim 24 in which said drug is a member selected from the group consisting of cyclosporine, digoxin, and doxifluridine.

26. A method in accordance with claim 24 in which said drug is doxifluridine.

27. A method of treating a subject undergoing an organ transplant to suppress an immune response to said transplant, by administering cyclosporine to said subject without substantial degradation of said cyclosporine by colonic bacterial enzymes residing in enterocytes of the lower gastrointestinal tract, said method comprising orally administering to said subject a dosage form of said cyclosporine while said subject is in a fed mode, said dosage form comprising a solid polymeric matrix with said cyclosporine dispersed therein at a weight ratio of cyclosporine to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said cyclosporine one hour after such immersion in gastric fluid, (d) releases substantially all of said cyclosporine within about ten hours after such immersion, and (e) remains substantially intact until all of said cyclosporine is released, thereby extending the release rate of said cyclosporine with time during said fed mode while releasing substantially all of said cyclosporine within said stomach and substantially avoiding contact of said cyclosporine with said colonic bacterial enzymes.

28. A method of treating a subject for heart disease by administering digoxin to said subject without substantial degradation of said digoxin by colonic bacterial enzymes residing in enterocytes of the lower gastrointestinal tract, said method comprising orally administering to said subject a dosage form of said digoxin while said subject is in a fed mode, said dosage form comprising a solid polymeric matrix with said digoxin dispersed therein at a weight ratio of digoxin to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said digoxin one hour after such immersion in gastric fluid,
(d) releases substantially all of said digoxin within about ten hours after such immersion, and
(e) remains substantially intact until all of said digoxin is released, thereby extending the release rate of said digoxin with time during said fed mode while releasing substantially all of said digoxin within said stomach and substantially avoiding contact of said digoxin with said colonic bacterial enzymes.

29. A method of treating a subject suffering from a condition selected from the group consisting of ovarian cancer, colorectal cancer, gastric cancer, renal cancer, and breast cancer, by administering doxifluridine to said subject without substantial degradation of said doxifluridine by intestinal enzymes or substantial inactivation of said doxifluridine by drug transporters residing in enterocytes of the lower gastrointestinal tract, said method comprising orally administering to said subject a dosage form of said doxifluridine while said subject is in a fed mode, said dosage form comprising a solid polymeric matrix with said doxifluridine dispersed therein at a weight ratio of doxifluridine to polymer of from about 0.01:99.99 to about 80:20, said polymeric matrix being one that:
    (a) swells upon imbibition of gastric fluid to a size large enough to promote retention in the stomach during said fed mode,
    (b) releases said drug into gastric fluid by the dissolving of said drug by said gastric fluid and either erosion of said matrix or diffusion of said dissolved drug out of said matrix,
    (c) retains at least about 40% of said doxifluridine one hour after such immersion in gastric fluid,
    (d) releases substantially all of said doxifluridine within about ten hours after such immersion, and
    (e) remains substantially intact until all of said doxifluridine is released, thereby extending the release rate of said doxifluridine with time during said fed mode while releasing substantially all of said doxifluridine within said stomach and substantially avoiding contact of said doxifluridine with said enzymes.

30. A method of administering to a subject a drug that is therapeutic to said subject when absorbed in the stomach but also susceptible to inactivation by drug transporters residing in lower gastrointestinal tract enterocytes, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:
    (a) swells upon imbibition of gastric fluid to a size large enough to promote retention in the stomach during said fed mode,
    (b) releases said drug into gastric fluid by the dissolving of said drug by said gastric fluid and either erosion of said matrix or diffusion of said dissolved drug out of said matrix,
    (c) retains at least about 40% of said drug one hour after such immersion in gastric fluid,
    (d) releases substantially all of said drug within about ten hours after such immersion, and
    (e) remains substantially intact until all of said drug is released, thereby extending the release rate of said drug with time during said fed mode while releasing substantially all of said drug within said stomach and substantially avoiding contact of said drug with said drug transporters.

31. A method in accordance with claim 30 in which said drug is a member selected from the group consisting of cyclosporine and paclitaxel.

32. A method of treating a subject undergoing an organ transplant to suppress an immune response to said transplant, by administering cyclosporine to said subject without substantial inactivation of said cyclosporine by p-glycoprotein in the lower gastrointestinal tract, said method comprising orally administering to said subject a dosage form of said cyclosporine while said subject is in a fed mode, said dosage form comprising a solid polymeric matrix with said cyclosporine dispersed therein at a weight ratio of cyclosporine to polymer of from about 0.01:99.99 to about 80:20, said polymeric matrix being one that:
    (a) swells upon imbibition of gastric fluid to a size large enough to promote retention in the stomach during said fed mode,
    (b) releases said drug into gastric fluid by the dissolving of said drug by said gastric fluid and either erosion of said matrix or diffusion of said dissolved drug out of said matrix,
    (c) retains at least about 40% of said cyclosporine one hour after such immersion in gastric fluid,
    (d) releases substantially all of said cyclosporine within about ten hours after such immersion, and
    (e) remains substantially intact until all of said cyclosporine is released, thereby extending the release rate of said cyclosporine with time during said fed mode while releasing substantially all of said cyclosporine within said stomach and substantially avoiding inactivation of said cyclosporine by p-glycoprotein in said lower gastrointestinal tract.

33. A method of treating a subject suffering from cancer by administering paclitaxel to said subject without substantial inactivation of said paclitaxel by p-glycoprotein in the lower gastrointestinal tract, said method comprising orally administering to said subject a dosage form of said paclitaxel while said subject is in a fed mode, said dosage form comprising a solid polymeric matrix with said paclitaxel dispersed therein at a weight ratio of paclitaxel to polymer of from about 0.01:99.99 to about 80:20, said polymeric matrix being one that:
    (a) swells upon imbibition of gastric fluid to a size large enough to promote retention in the stomach during said fed mode,
    (b) releases said drug into gastric fluid by the dissolving of said drug by said gastric fluid and either erosion of said matrix or diffusion of said dissolved drug out of said matrix,
    (c) retains at least about 40% of said paclitaxel one hour after such immersion in gastric fluid,
    (d) releases substantially all of said paclitaxel within about ten hours after such immersion, and
    (e) remains substantially intact until all of said paclitaxel is released, thereby extending the release rate of said paclitaxel with time during said fed mode while releasing substantially all of said paclitaxel within said stomach and substantially avoiding inactivation of said paclitaxel by p-glycoprotein in said lower gastrointestinal tract.

34. A method of administering to a subject a drug that is therapeutic to said subject when absorbed in the stomach and whose bioavailability is substantially greater in an acidic environment than an alkaline environment, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach where said drug is maintained in an acidic environment.

35. A method in accordance with claim 34 in which said drug is a member selected from the group consisting of esters of ampicillin, iron salts, digoxin, and ketoconazole.

36. A method in accordance with claim 34 in which said drug is a member selected from the group consisting of esters of ampicillin.

37. A method of treating a subject suffering from a bacterial infection by administering an ester of ampicillin to said subject while maintaining maximum bioavailability of said ester of ampicillin, said method comprising orally administering to said subject a dosage form of said ester of ampicillin while said subject is in a fed mode, said dosage form comprising a solid polymeric matrix with said ester of ampicillin dispersed therein at a weight ratio of said ester of ampicillin to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said ester of ampicillin one hour after such immersion in gastric fluid, (d) releases substantially all of said ester of ampicillin within about ten hours after such immersion, and (e) remains substantially intact until all of said ester of ampicillin is released, thereby extending the release rate of said ester of ampicillin with time during said fed mode while releasing substantially all of said ester of ampicillin within said stomach and maintaining said ester of ampicillin in the acidic environment of said stomach during said release.

38. A method of treating a subject suffering from anemia by administering iron salts to said subject while maintaining maximum bioavailability of said iron salts, said method comprising orally administering to said subject a dosage form of said iron salts while said subject is in a fed mode, said dosage form comprising a solid polymeric matrix with said iron salts dispersed therein at a weight ratio of iron salts to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said iron salts one hour after such immersion in gastric fluid, (d) releases substantially all of said iron salts within about ten hours after such immersion, and (e) remains substantially intact until all of said iron salts is released, thereby extending the release rate of said iron salts with time during said fed mode while releasing substantially all of said iron salts within said stomach where said iron salts are maintained in an acidic environment.

39. A method of treating a subject suffering from a systemic fungal infection by administering ketoconazole to said subject while maintaining maximum bioavailability of said ketoconazole, said method comprising orally administering to said subject a dosage form of said ketoconazole while said subject is in a fed mode, said dosage form comprising a solid polymeric matrix with said ketoconazole dispersed therein at a weight ratio of ketoconazole to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said ketoconazole one hour after such immersion in gastric fluid, (d) releases substantially all of said ketoconazole within about ten hours after such immersion, and (e) remains substantially intact until all of said ketoconazole is released, thereby extending the release rate of said ketoconazole with time during said fed mode while releasing substantially all of said ketoconazole within said stomach where said ketoconazole is maintained in an acidic environment.

40. A method of administering to a subject a drug that is therapeutic to said subject when absorbed in the stomach but also degradable in an alkaline environment, said method comprising orally administering to said subject a dosage form of said drug while said subject is in a fed mode, said dosage form comprising a solid polymeric matrix in which said drug is dispersed at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach where said drug is maintained in an acidic environment.

41. A method in accordance with claim 40 in which said drug is nelfinar mesylate.

42. A method of treating a subject infected with human immunodeficiency virus by administering nelfinar mesylate to said subject without substantial degradation of said nelfinar mesylate by intestinal flora or substantial inactivation of said nelfinar mesylate by drug transporters residing in enterocytes of the lower gastrointestinal tract, said method comprising orally administering to said subject a dosage form of said nelfinar mesylate while said subject is in a fed mode, said dosage form comprising a solid polymeric matrix with said nelfinar mesylate dispersed therein at a weight ratio of nelfinar mesylate to polymer of from about 0.01:99.99 to about 80:20, said polymeric matrix being one that:

(a) swells upon imbibition of gastric fluid to a size large enough to promote retention in the stomach during said fed mode, (b) releases said nelfinar mesylate into gastric fluid by the dissolving of said nelfinar mesylate by said gastric fluid and either erosion of said matrix or diffusion of said dissolved nelfinar mesylate out of said matrix, (c) retains at least about 40% of said nelfinar mesylate one hour after such immersion in gastric fluid, (d) releases substantially all of said nelfinar mesylate within about ten hours after such immersion, and (e) remains substantially intact until all of said nelfinar mesylate is released, thereby extending the release rate of said nelfinar mesylate with time during said fed mode while releasing substantially all of said nelfinar mesylate within said stomach where said nelfinar mesylate is maintained in an acidic environment.

43. A method of administering to a subject a drug that is therapeutic to said subject when absorbed in the stomach where said drug has at least one ionized group in the pH range 5 through 8, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) retains at least about 40% of said drug one hour after such immersion in gastric fluid, (d) releases substantially all of said drug within about ten hours after such immersion, and (e) remains substantially intact until all of said drug is released, thereby extending the release rate of said drug with time during said fed mode while releasing substantially all of said drug within said stomach where said drug is maintained in an acidic environment.

44. A method of administering to a subject a drug that is therapeutic to said subject when absorbed in the stomach but also degradable in an acidic environment, said method comprising orally administering to said subject a dosage form of said drug while said subject is in a fed mode, said dosage form comprising a solid polymeric matrix with said drug dispersed therein at a weight ratio of drug to polymer of from about 0.01:99.99 to about 80:20, said polymeric matrix being one that:

(a) swells upon imbibition of gastric fluid to a size large enough to promote retention in the stomach during said fed mode, (b) releases said drug into gastric fluid by the dissolving of said drug by said gastric fluid and either erosion of said matrix or diffusion of said dissolved drug out of said matrix, (c) protects any unreleased drug in said matrix from said gastric fluid, (d) retains at least about 40% of said drug one hour after such immersion in gastric fluid, (e) releases substantially all of said drug within about ten hours after such immersion, and (f) remains substantially intact until all of said drug is released, thereby extending the release rate of said drug with time during said fed mode while releasing substantially all of said drug within said stomach where said drug is maintained in an acidic environment.

45. A dosage form of claim 1 in which said drug is metformin hydrochloride and said solid polymeric matrix comprises an alkyl-substituted cellulose.

46. A dosage form of claim 1 in which said drug is metformin hydrochloride and said solid polymeric matrix comprises hydroxypropylmethyl cellulose.

47. A dosage form of claim 1 in which said drug is metformin hydrochloride and said solid polymeric matrix comprises poly(ethylene oxide) at a molecular weight of from about 4,500,000 to about 10,000,000.

48. A method in accordance with claim 19 in which said solid polymeric matrix comprises poly(ethylene oxide) at a molecular weight of at least about 4,000,000.

49. A method in accordance with claim 19 in which said solid polymeric matrix comprises poly(ethylene oxide) at a molecular weight of from about 4,500,000 to about 10,000,000.

50. A method in accordance with claim 19 in which said solid polymeric matrix comprises an alkyl-substituted cellulose.

51. A method in accordance with claim 19 in which said solid polymeric matrix comprises hydroxypropylmethyl cellulose.

52. A method in accordance with claim 43 in which said drug is a member selected from the group consisting of metformin hydrochloride, lisinopril, captopril, buprorion, ganciclovir, and iron salts.

53. A method in accordance with claim 43 in which said drug is metformin hydrochloride.

54. A method in accordance with claim 43 in which said solid polymeric matrix comprises poly(ethylene oxide) at a molecular weight of at least about 4,000,000.

55. A method in accordance with claim 43 in which said solid polymeric matrix comprises poly(ethylene oxide) at a molecular weight of from about 4,500,000 to about 10,000,000.

56. A method in accordance with claim 43 in which said drug is metformin hydrochloride and said solid polymeric matrix comprises poly(ethylene oxide) at a molecular weight of at least about 4,000,000.

57. A method in accordance with claim 43 in which said solid polymeric matrix comprises an alkyl-substituted cellulose.

58. A method in accordance with claim 43 in which said solid polymeric matrix comprises hydroxypropylmethyl cellulose.

59. A method in accordance with claim 43 in which said drug is metformin hydrochloride and said solid polymeric matrix comprises an alkyl-substituted cellulose.

60. A method in accordance with claim 43 in which said drug is metformin hydrochloride and said solid polymeric matrix comprises hydroxypropylmethyl cellulose.

61. A dosage form of claim 1 in which said polymeric matrix is comprised of hydroxypropylmethylcellulose.

62. A dosage form of claim 1 in which said polymeric matrix is comprised of hydroxypropylmethylcellulose with a viscosity range of 11,000 to 110,000 centipoise as measured in a 2% solution at 20° C.

63. A dosage form of claim 1 in which said drug is metformin hydrochloride and said polymeric matrix is comprised of hydroxypropylmethylcellulose with a viscosity range of 11,000 to 110,000 centipoise as measured in a 2% solution at 20° C.

64. A dosage form of claim 1 in which said drug is metformin hydrochloride and said polymeric matrix is comprised of an alkyl-substituted cellulose.

65. A dosage form of claim 1 in which said drug is metformin hydrochloride and said polymeric matrix is comprised of hydroxypropylmethylcellulose.

66. A method in accordance with claim 43 in which said polymeric matrix is comprised of hydroxypropylmethylcellulose with a viscosity range of 11,000 to 110,000 centipoise as measured in a 2% solution at 20° C.

67. A method in accordance with claim 43 in which said drug is metformin hydrochloride and said polymeric matrix is comprised of hydroxypropylmethylcellulose with a viscosity range of 11,000 to 110,000 centipoise as measured in a 2% solution at 20° C.

68. A controlled-release oral drug dosage form for releasing metformin hydrochloride, said dosage form comprising a solid polymeric matrix with said metformin hydrochloride therein at a weight ratio of drug to polymer of from about 15:85 to about 80:20, said polymeric matrix being one that swells upon imbibition of water thereby attaining a size large enough to promote retention in the stomach during the fed mode, that releases said metformin hydrochloride into gastric fluid by the dissolution and diffusion of said metformin hydrochloride out of said matrix by said gastric fluid, and that upon immersion in gastric fluid retains at least about 40% of said metformin hydrochloride one hour after such immersion.

69. The dosage form of claim 68, wherein said polymeric matrix comprises a polymer selected from the group consisting of poly(ethylene oxide), cellulose, alkyl-substituted celluloses, crosslinked polyacrylic acids, and xanthum gum.

70. The dosage form of claim 69, wherein said polymeric matrix comprises an alkyl-substituted cellulose.

71. The dosage form of claim 70, wherein said polymeric matrix comprises an alkyl-substituted cellulose selected from the group consisting of hydroxymethyl-cellulose, hydroxyethyl-cellulose, hydroxypropyl-cellulose, hydroxypropylmethyl-cellulose, and carboxymethyl-cellulose.

72. The dosage form of claim 71, wherein said polymeric matrix comprises hydroxypropylmethyl-cellulose.

73. The dosage form of claim 71, wherein said polymeric matrix comprises hydroxypropylmethyl-cellulose having a viscosity ranging from 11,000 to 110,000 centipoise as measured in a 2% solution at 20 C.

74. The dosage form of claim 68, wherein said polymeric matrix upon immersion in gastric fluid retains at least about 50% of said metformin hydrochloride one hour after such immersion.

75. The dosage form of claim 68, wherein said polymeric matrix upon immersion in gastric fluid retains at least about 60% of said metformin hydrochloride one hour after such immersion.

76. The dosage form of claim 68, wherein said polymeric matrix comprises poly(ethylene oxide) having a molecular weight of at least about 4,000,000.

77. The dosage form of claim 68, wherein said polymeric matrix comprises poly(ethylene oxide) having a molecular weight ranging from about 4,500,000 to about 10,000,000.

78. The dosage form of claim 68, wherein said polymeric matrix comprises poly(ethylene oxide) having a molecular weight ranging from about 5,000,000 to about 8,000,000.

79. A controlled-release oral drug dosage form for releasing metformin hydrochloride, said dosage form comprising a solid polymeric matrix tablet with said metformin hydrochloride therein at a weight ratio of drug to polymer of from about 15:85 to about 80:20, said polymeric matrix tablet being one that swells upon imbibition of water thereby attaining a size large enough to promote retention in the stomach during the fed mode, that releases said metformin hydrochloride into gastric fluid by the dissolution and diffusion of said metformin hydrochloride out of said matrix by said gastric fluid, and that upon immersion in gastric fluid retains at least about 40% of said metformin hydrochloride one hour after such immersion.

80. The dosage form of claim 79, wherein said polymeric matrix of said polymeric matrix tablet comprises a polymer selected from the group consisting of poly(ethylene oxide), cellulose, alkyl-substituted celluloses, crosslinked polyacrylic acids, and xanthum gum.

81. The dosage form of claim 80, wherein said polymeric matrix comprises an alkyl-substituted cellulose.

82. The dosage form of claim 81, wherein said polymeric matrix comprises an alkyl-substituted cellulose selected from the group consisting of hydroxymethyl-cellulose, hydroxyethyl-cellulose, hydroxypropyl-cellulose, hydroxypropylmethyl-cellulose, and carboxymethyl-cellulose.

83. The dosage form of claim 82, wherein said polymeric matrix comprises hydroxypropylmethyl-cellulose.

84. The dosage form of claim 83, wherein said polymeric matrix comprises hydroxypropylmethyl-cellulose having a viscosity ranging from 11,000 to 110,000 centipoise as measured in a 2% solution at 20 C.

85. The dosage form of claim 79, wherein said polymeric matrix tablet upon immersion in gastric fluid retains at least about 50% of said metformin hydrochloride one hour after such immersion.

86. The dosage form of claim 79, wherein said polymeric matrix tablet upon immersion in gastric fluid retains at least about 60% of said metformin hydrochloride one hour after such immersion.

87. The dosage form of claim 79, wherein said polymeric matrix of said polymeric matrix tablet comprises poly(ethylene oxide) having a molecular weight of at least about 4,000,000.

88. The dosage form of claim 79, wherein said polymeric matrix of said polymeric matrix tablet comprises poly(ethylene oxide) having a molecular weight ranging from about 4,500,000 to about 10,000,000.

89. The dosage form of claim 79, wherein said polymeric matrix of said polymeric matrix tablet comprises poly(ethylene oxide) having a molecular weight ranging from about 5,000,000 to about 8,000,000.

* * * * *